United States Patent
Russell et al.

(10) Patent No.: US 11,680,057 B2
(45) Date of Patent: Jun. 20, 2023

(54) PYRAZOLE DERIVATIVES

(71) Applicant: SYNGENTA CROP PROTECTION AG, Basel (CH)

(72) Inventors: Sally Elizabeth Russell, Bracknell (GB); James Alan Morris, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

(21) Appl. No.: 17/161,788

(22) Filed: Jan. 29, 2021

(65) Prior Publication Data
US 2021/0147389 A1 May 20, 2021

Related U.S. Application Data

(62) Division of application No. 16/782,796, filed on Feb. 5, 2020, now Pat. No. 11,059,806.

(30) Foreign Application Priority Data

Feb. 5, 2019 (GB) ..................................... 1901559

(51) Int. Cl.
| | | |
|---|---|---|
| C07D 207/337 | (2006.01) | |
| C07D 207/34 | (2006.01) | |
| C07D 207/325 | (2006.01) | |
| A01N 43/54 | (2006.01) | |
| A01N 43/58 | (2006.01) | |
| A01N 43/80 | (2006.01) | |
| A01N 43/90 | (2006.01) | |
| A01N 43/56 | (2006.01) | |
| C07D 403/04 | (2006.01) | |
| C07D 401/04 | (2006.01) | |
| C07D 401/14 | (2006.01) | |
| C07D 409/14 | (2006.01) | |
| C07D 413/04 | (2006.01) | |
| C07D 471/04 | (2006.01) | |
| C07D 487/04 | (2006.01) | |

(52) U.S. Cl.
CPC .......... *C07D 403/04* (2013.01); *A01N 43/54* (2013.01); *A01N 43/56* (2013.01); *A01N 43/58* (2013.01); *A01N 43/80* (2013.01); *A01N 43/90* (2013.01); *C07D 207/325* (2013.01); *C07D 207/337* (2013.01); *C07D 207/34* (2013.01); *C07D 401/04* (2013.01); *C07D 401/14* (2013.01); *C07D 409/14* (2013.01); *C07D 413/04* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 5,763,470 | A | 6/1998 | Tang et al. |
| 7,312,350 | B2 * | 12/2007 | Ebenbeck ............ C07D 231/12 558/56 |
| 7,423,159 | B2 * | 9/2008 | Momose .................. A61P 9/04 548/356.1 |
| 10,294,202 | B2 | 5/2019 | Satterfield et al. |
| 2004/0142820 | A1 | 1/2004 | Ebenbeck et al. |
| 2006/0127396 | A1 | 6/2006 | Ito et al. |
| 2007/0123508 | A1 | 5/2007 | Olsson et al. |
| 2013/0317003 | A1 | 11/2013 | Jacques et al. |
| 2019/0169153 | A1 | 6/2019 | Dugar et al. |

FOREIGN PATENT DOCUMENTS

| | | |
|---|---|---|
| CN | 104844519 A | 8/2015 |
| WO | 2012118782 A1 | 9/2012 |
| WO | 2015084796 A1 | 6/2015 |
| WO | 2018065311 A1 | 4/2018 |
| WO | 2018177836 A1 | 10/2018 |
| WO | 2018177837 A1 | 10/2018 |
| WO | 2019025156 A1 | 2/2019 |

OTHER PUBLICATIONS

CAS Registry Entry 1564032-97-8 (2014).*
CAS Registry Entry 2304324-51-2, Entered Apr. 10, 2019.*
Barnes, David M et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J. Am. Chem. Soc., Oct. 15, 2002, vol. 124, pp. 3097-13105.
Evans, David A. et al., "Ni(II)-Bis[(R,R)-N,N"-dibenzylcyclohexane-1,2-diamine]Br2 Catalyzed Enantioselective Michael Additions of 1,3-Dicarbonyl Compounds to Conjugated Nitroalkenes", J. Am. Chem. Soc., Jun. 23, 2005 (online), vol. 127, pp. 9958-9959.

(Continued)

*Primary Examiner* — Joseph R Kosack
(74) *Attorney, Agent, or Firm* — BakerHostetler; Toni-Junell Herbert

(57) ABSTRACT

The present invention relates to pyrazole derivatives of formula (X)

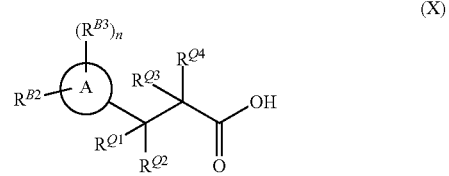

wherein ring A is a pyrazole and substituents $R^{B1}$, $R^{B2}$, n, $R^{Q1}$, $R^{Q2}$, $R^{Q3}$, and $R^{Q4}$ are as defined in claim 1, their manufacture, and their use in the manufacture of agrochemicals and pharmaceuticals.

10 Claims, No Drawings

(56) References Cited

OTHER PUBLICATIONS

International Search Report and Written Opinion for International Application No. PCT/EP2020/052780 dated Mar. 30, 2020.
U.S. Appl. No. 16/782,530, filed Feb. 5, 2020 (Russell et al.).
U.S. Appl. No. 16/782,866, filed Feb. 5, 2020 (Morris et al.).
U.S. Appl. No. 16/874,136, filed May 14, 2020 (Morris et al.).
U.S. Appl. No. 16/874,165, filed May 14, 2020 (Morris et al.).
U.S. Appl. No. 16/874,715, filed May 15, 2020 (Morris et al.).
PGR2020-00028 Decision Granting Institution of Post-Grant Review; *Syngenta Crop Protection AG* v. *FMC Corporation*, dated Sep. 15, 2020.
Vineeta Garg et al: "Chemo-, Regio-, and Stereoselective N-Alkenylation of Pyrazoles/Benzpyrazoles Using Activated and Unactivated Alkynes" The Journal of Organic Chemistry, vol. 82, No. 19, pp. 10247-10262 (Sep. 1, 2017).
Ryabukhin et al. "Toward Lead-Oriented Synthesis: One-Pot Version of Castagnoli Condensation with Nonactivated Alicyclic Anhydrides" ACS Combinatorial Science, 2014, vol. 16, No. 3, pp. 146-153.

\* cited by examiner

PYRAZOLE DERIVATIVES

CROSS-REFERENCE TO RELATED APPLICATIONS

This application is a divisional of U.S. application Ser. No. 16/782,796, filed Feb. 5, 2020, which claims priority to Patent Application No. GB1901559.3 filed in the United Kingdom on Feb. 5, 2019, the entire contents of all of which are incorporated herein by reference.

The present invention relates to pyrazole derivatives of formula (X) as described herein, which are valuable intermediates in the production of agrochemicals and pharmaceuticals. The invention extends to the manufacture of such pyrazole derivatives, and their subsequent use in the manufacture of agrochemicals and/or pharmaceuticals.

In a first aspect the invention provides a compounds of formula (X)

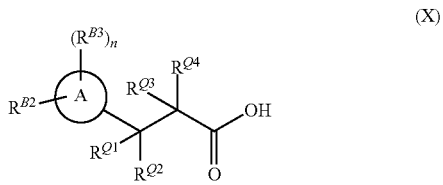

(X)

wherein ring A as is a di- or tri-substituted pyrazole, substituted on one ring nitrogen by $R^{B2}$ and substituted on at least one ring carbon by $R^{B3}$, wherein $R^{B2}$ is $C_1$-$C_3$ alkyl or $C_1$-$C_3$fluoroalkyl, n is an integer of 1 or 2 and each $R^{B3}$ is independently halogen, $C_1$-$C_3$fluoroalkyl, $C_1$-$C_3$haloalkoxy, $C_1$-$C_3$alkoxy, $C_1$-$C_3$haloalkyl, $C_1$-$C_3$fluoroalkyl, $C_1$-$C_3$haloalkoxy, $C_1$-$C_3$alkoxy, or $C_1$-$C_3$alkyl; $R^{Q1}$ and $R^{Q4}$ are each hydrogen, and $R^{Q2}$ and $R^{Q3}$ together with the carbon atoms to which they are joined form ring Q, which is an optionally substituted 5-membered thio-lactam ring.

In a second aspect, there is provided a process for the production of a compound of formula (X) defined above, in which ring Q is substituted by $R^1$, said process comprising:
(i) reacting a compound of formula (A) with ethyl acrylate, under palladium catalysis to give a compound of formula (B)

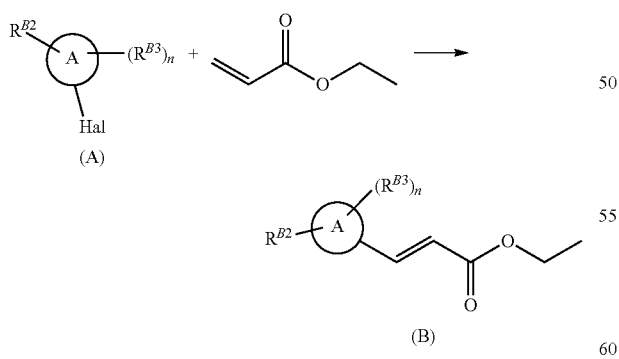

wherein ring A is a pyrazole ring substituted on a ring carbon by Hal, Hal is iodo, bromo or chloro, $R^{B2}$ is a substituent on a ring nitrogen and is $C_1$-$C_3$ alkyl or $C_1$-$C_3$fluoroalkyl, n is an integer of 1 or 2, $R^{B3}$ is a substituent on a ring carbon and each $R^{B3}$ is independently halogen, $C_1$-$C_3$fluoroalkyl, $C_1$-$C_3$haloalkoxy, $C_1$-$C_3$alkoxy, $C_1$-$C_3$haloalkyl, $C_1$-$C_3$fluoroalkyl, $C_1$-$C_3$haloalkoxy, $C_1$-$C_3$alkoxy, or $C_1$-$C_3$alkyl;

(ii) reacting the compound of formula (B) from step (i) with a compound of formula (C),

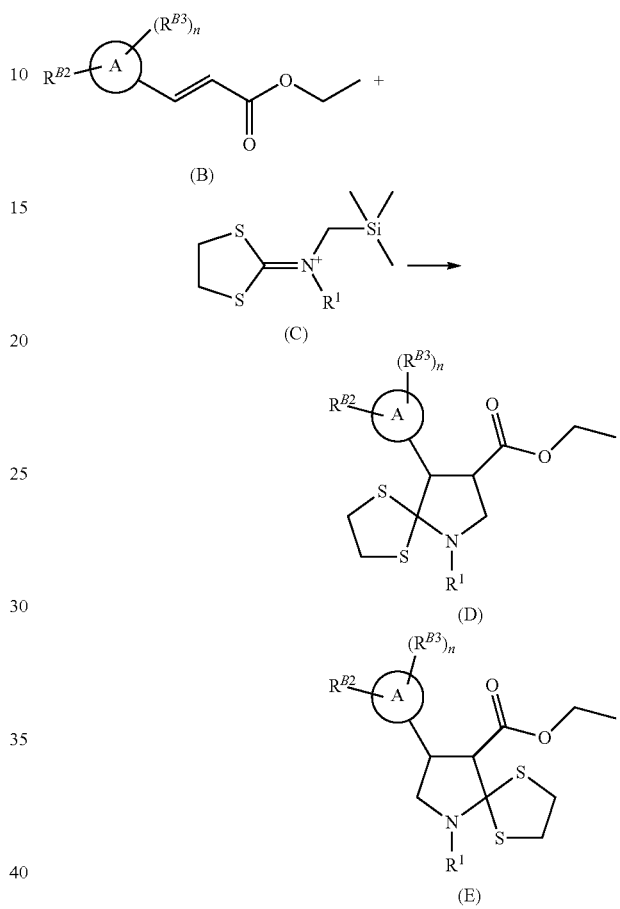

wherein $R^1$ is selected from the group consisting of $C_1$-$C_6$ alkyl, $C_2$-$C_6$alkenyl, $C_3$-$C_6$cycloalkyl, $C_3$-$C_6$cycloalkenyl, optionally substituted phenyl, optionally substituted $C_5$-$C_6$ heteroaryl, —$CR^{12}R^{13}$, —$C(O)R^{12}$; $R^{12}$ is hydrogen, OH, $C_1$-$C_3$ alkoxy, or $C_1$-$C_4$ alkyl; $R^{13}$ is —$C(O)NH_2$;

in a cycloaddition reaction to yield a mixture of compounds of formula (D) and (E);

(iii) reacting the compound of formula (E) with a hydroxide base in a water/ether mixed solvent system to give the compound of formula (X)

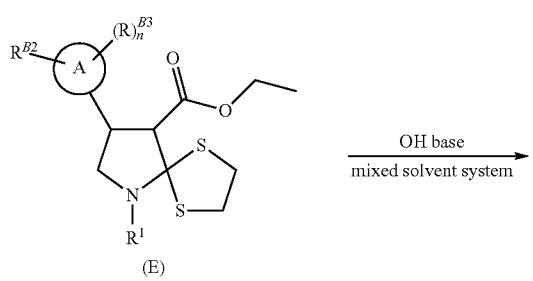

-continued

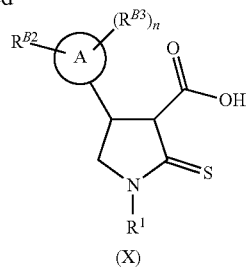

(X)

wherein A, $R^{B2}$, $R^{B3}$, n and $R^1$ are as defined in steps (i) and (ii) above.

Compounds of formula (B), (D) and (E) are also novel and form yet further aspects of the invention.

As used herein, the term "halogen" or "halo" refers to fluorine (fluoro), chlorine (chloro), bromine (bromo) or iodine (iodo), preferably fluorine, chlorine or bromine unless otherwise stated.

As used herein, cyano means a —CN group.

As used herein, hydroxy means an —OH group.

As used herein, nitro means an —$NO_2$ group.

Each alkyl moiety either alone or as part of a larger group (such as alkoxy, alkylthio, haloalkyl, haloalkoxy et al.) may be straight-chained or branched, and as used herein the term specifically also includes cyclopropyl. Typically, the alkyl is, for example, methyl, ethyl, n-propyl, cyclopropyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1$ or $C_2$alkyl groups (i.e. methyl or ethyl).

As used herein, the term "$C_1$-$C_3$alkoxy" refers to a radical of the formula —$OR_a$ where $R_a$ is a $C_1$-$C_3$alkyl radical as generally defined above. Examples of $C_1$-$C_3$alkoxy thus include methoxy, ethoxy, propoxy, and iso-propoxy.

As used herein, the term "$C_1$-$C_3$haloalkyl" refers to a $C_1$-$C_3$alkyl radical as generally defined above substituted by one or more of the same or different halogen atoms. Examples of $C_1$-$C_3$haloalkyl thus include, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

As used herein, the term "$C_1$-$C_3$haloalkoxy" refers to a $C_1$-$C_3$alkoxy group as defined above substituted by one or more of the same or different halogen atoms. Examples of $C_1$-$C_3$haloalkoxy thus include, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy.

The term "$C_1$-$C_6$alkylthio" refers to the group $C_1$-$C_6$alkyl-S—, and is, for example, methylthio, ethylthio, propylthio, isopropylthio, n-butylthio, isobutylthio, sec-butylthio or tert-butylthio, preferably methylthio or ethylthio.

The term "$C_1$-$C_6$alkylsulfinyl" refers to the group $C_1$-$C_6$alkyl-S(O)—, and is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

The term "$C_1$-$C_6$alkylsulfonyl" refers to the group $C_1$-$C_6$alkyl-S(O)$_2$—, and is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The compounds of formula (X) may exist as different geometric isomers, or in different tautomeric forms. This invention covers the use of all such isomers and tautomers, and mixtures thereof in all proportions, as well as isotopic forms such as deuterated compounds. They may contain one or more asymmetric centers and may thus give rise to optical isomers and diastereomers. While shown for formula (X) without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof. It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

Similarly, presence of one or more possible asymmetric carbon atoms in compound of formulae (D), (E), (H) and (I) means that these compounds may also occur in chiral isomeric forms, i.e., enantiomeric or diastereomeric forms. Also, atropisomers may occur as a result of restricted rotation about a single bond. Formulae (D), (E), (H) and (I) are intended to include all those possible isomeric forms and mixtures thereof. The present invention includes the use of all those possible isomeric forms and mixtures thereof for compounds of formulae (D), (E), (H) and (I) Likewise, formula (D), (E), (H) and (I) are intended to include all possible tautomers (including lactam-lactim tautomerism and keto-enol tautomerism) where present. The present invention thus includes the use of all possible tautomeric forms for compounds of formula (D), (E), (H) and (I).

Suitable salts include those derived from alkali or alkaline earth metals and those derived from ammonia and amines. Preferred cations include sodium, potassium, magnesium, and ammonium cations of the formula $N^+(R^{119}R^{120}R^{121}R^{122})$ wherein $R^{119}$, $R^{120}$, $R^{121}$ and $R^{122}$ are independently selected from hydrogen, $C_1$-$C_6$ alkyl and $C_1$-$C_6$ hydroxyalkyl. Salts of the compounds of formula (I) can be prepared by treatment of compounds of formula (I) with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of formula (I) because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The present invention is based on the following generalized reaction scheme, in which ring A, $R^{B2}$, $R^{B3}$, n, $R^1$ and $R^2$ are as defined herein.

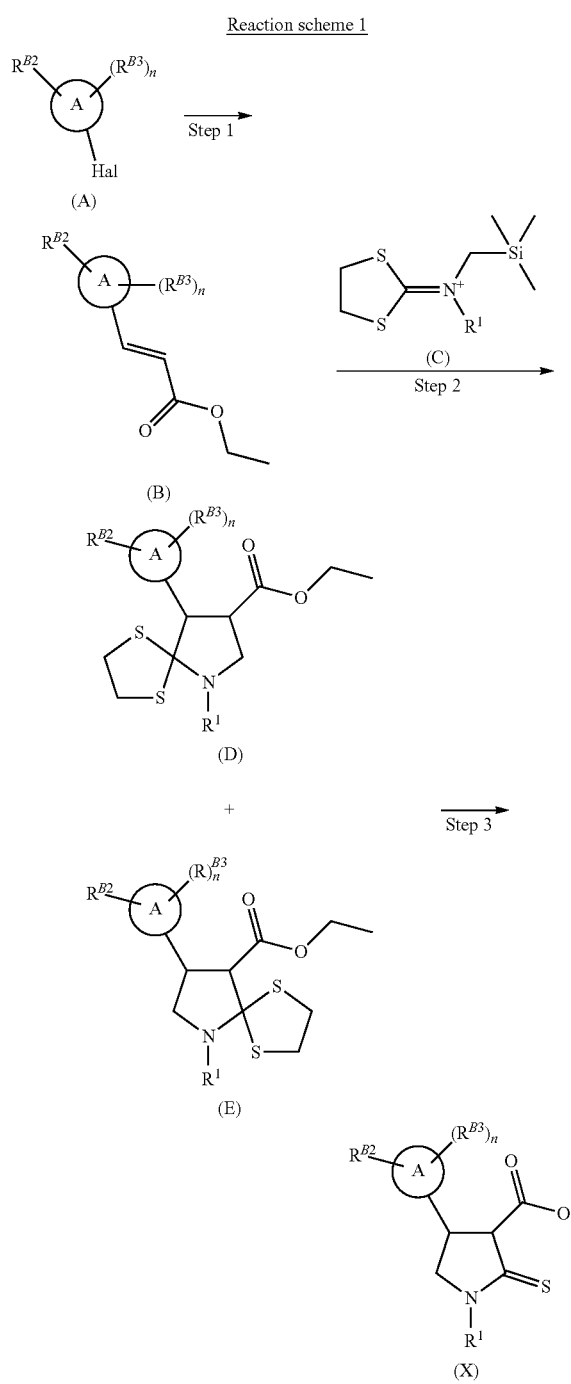

The desired halogenated pyrazole (A) is reacted with ethyl acrylate, under palladium catalysis, to afford the substituted vinyl pyrazole of formula (B). The substituted vinyl pyrazole (B) undergoes a cycloaddition with a dithiolane-isocyanate iminium methylide of formula (C) affording a mixture of pyrrolidine cycloadducts i.e. compounds of formula (D) and compounds of formula (E), which can be separated by chromatography. The desired pyrrolidine cycloadduct (in the above reaction scheme, the compound of formula (E) is exemplified) is reacted with a hydroxide base, in a water/ether mixed solvent system to afford the 3-carboxyl substituted thiolactam of formula (X). Compounds of formula (C) can be prepared as described in *Tetrahedron Lett.* 1995, 36:9409. Halogenated pyrazoles of formula (A) are either known or can be prepared according to methods well known in the art.

Depending upon the desired ultimate end-product, the 3-carboxyl-substituted thiolactam may be coupled with an aniline of formula (G) to afford the desired thiolactam-carboxamide of formula (H) using standard amide coupling conditions, such as propanephosphonic acid anhydride in a suitable solvent, such as dichloromethane, with a suitable base, as shown in Reaction Scheme 2 below. The skilled man will appreciate that the choice of $R^2$ is dependent upon the desired ultimate end product, and as such can be any suitable substituent that may be amide-linked.

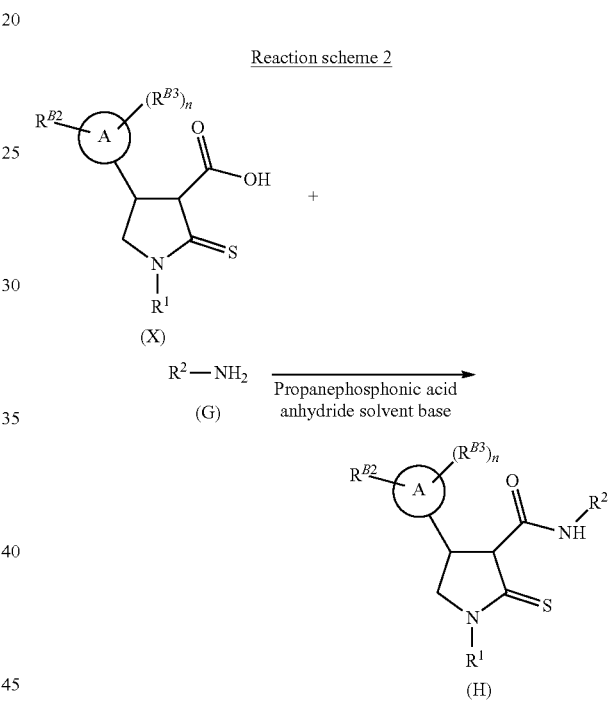

The resulting thiolactam-carboxamide of formula (H) may subsequently undergo oxidative hydrolysis, with hydrogen peroxide solution and a suitable acid to form a lactam compound of formula (I) (Reaction Scheme 3).

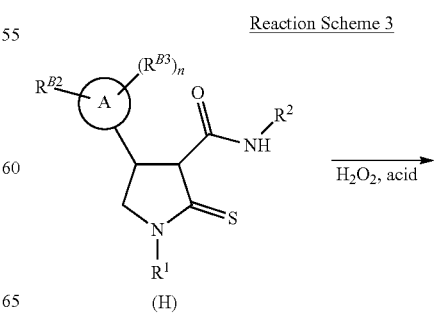

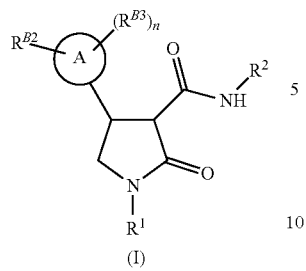

(I)

Alternatively the 3-carboxyl-substituted thiolactam of formula (X) may subsequently undergo oxidative hydrolysis, with hydrogen peroxide solution and a suitable acid to form a lactam compound of formula (J) as shown in Reaction Scheme 4. This may subsequently be coupled with an aniline of formula (G) to afford the desired lactam compound of formula (H) using standard amide coupling conditions as described above (see Reaction Scheme 5 below).

Reaction Scheme 4

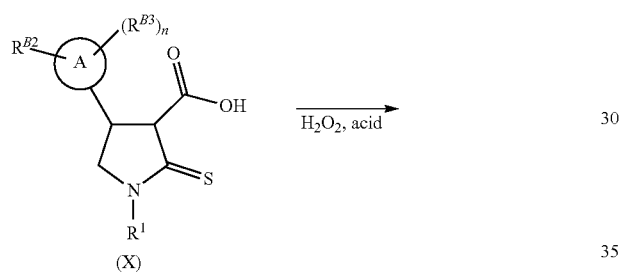

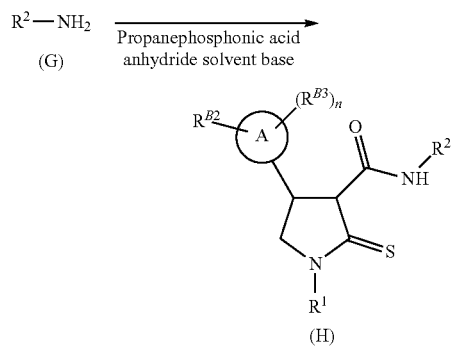

(H)

Single enantiomers can be prepared by chiral separation if desired. The skilled man will appreciate that compounds of formulae (D), (E), (X), (H), (I), and (J) may exist in different enantiomeric forms, for example:

(i) for a compound of formula (D)

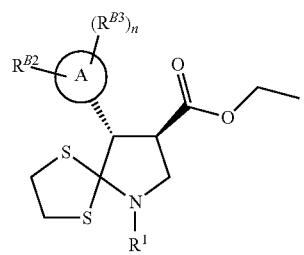

(D1)

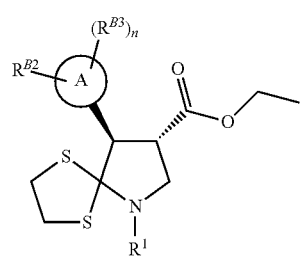

(D2)

(ii) for a compound of formula (E)

Reaction Scheme 5

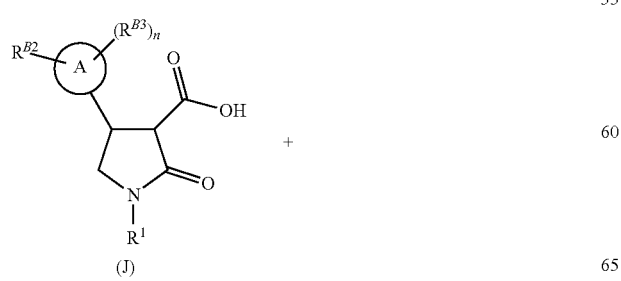

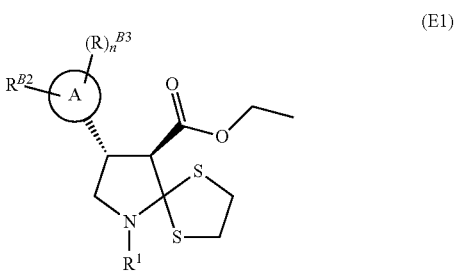

(E1)

-continued

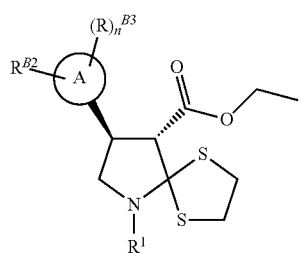

(E2)

(iii) for a compound of formula (X)

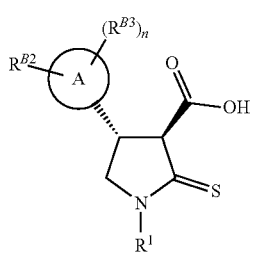

(X1)

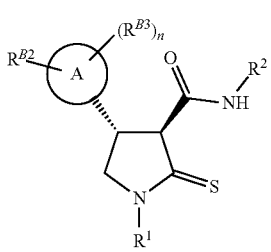

(X2)

(iv) for a compound of formula (H)

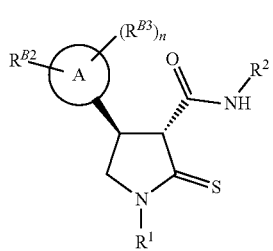

(H1)

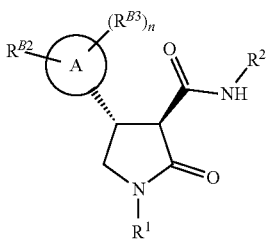

(H2)

(v) for a compound of formula (I)

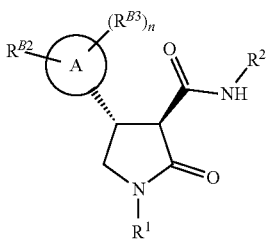

(I1)

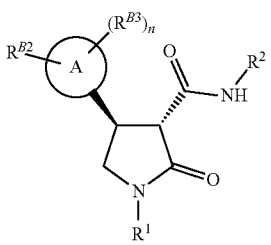

(I2)

(vi) for a compound of formula (J)

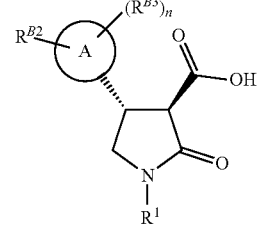

(J1)

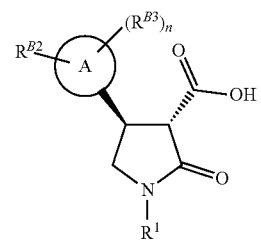

(J2)

In each case, in one set of embodiments, the following enantiomers are preferred (D1), (E1), (X1), (H1), (I1), and (J1).

In compounds of formulae (A), (B), (D), (E), (X), (H), and (I) as described herein, ring A is a pyrazole moiety carrying at least two substituents, wherein one of said substituents ($R^{B2}$) is borne by a ring nitrogen, and a second substituent ($R^{B3}$) is borne on a ring carbon atom. Clearly with such a configuration, A is carbon linked to the rest of the molecule.

When A is di-substituted and $R^{B3}$ is borne on the ring carbon atom adjacent the substituted ring nitrogen atom said $R^{B3}$ substituent may be defined as $R^{B3SN}$. For the avoidance of doubt $R^{B3SN}$ is a sub-definition of $R^{B3}$ used purely to denote positional placement within the pyrazole moiety, and therefore $R^{B3SN}$ is also selected from the group consisting of halogen, $C_1$-$C_3$fluoroalkyl, $C_1$-$C_3$haloalkoxy, $C_1$-$C_3$alkoxy, and $C_1$-$C_3$alkyl. Thus when A is di-substituted, it may be represented by groups $A^1$, $A^2$, $A^3$, $A^4$, or $A^5$, as shown below, wherein $R^{B2}$, $R^{B3}$ and $R^{B3SN}$ are as defined above and the jagged line denotes the point of attachment to the rest of the relevant molecule. In compounds of formula (A), this is to the relevant halogen atom. In compounds of formula (B) this is to the ethyl-propenoate moiety. In compounds of formulae (D) and (E), this is to the 1,4-dithia-6-azaspiro[4.4]nonane-8-carboxylate moiety. In compounds of formulae (X) (H) and (I) this is through the carbon atom at the 4-position of the (thio)lactam ring.

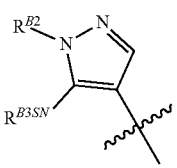
A¹

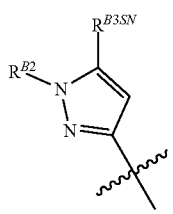
A²

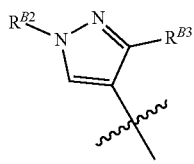
A³

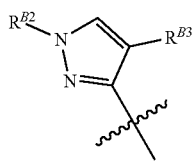
A⁴

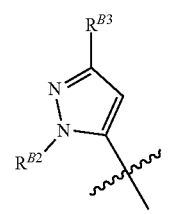
A⁵

Groups A¹ and A² are particularly preferred, with A² being the most preferred of the di-substituted pyrazoles Where ring A is tri-substituted it may be represented by groups A⁶ or A⁷ wherein the third substituent (R^{B3}) is also borne on a ring carbon atom:

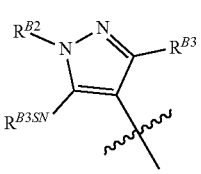
A⁶

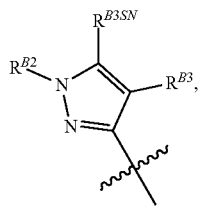
A⁷ wherein $R^{B2}$, $R^{B3}$ and $R^{B3SN}$ and the jagged line are as defined above.

Preferably $R^{B2}$ is selected from the group consisting of methyl, ethyl, n-propyl, fluoromethyl, trifluoromethyl, fluoroethyl, difluoroethyl and trifluoroethyl. More preferably $R^{B2}$ is selected from the group consisting of methyl, ethyl, n-propyl, trifluoromethyl and difluoroethyl. More preferably still, $R^{B2}$ is selected from the group consisting of methyl, ethyl, and difluoroethyl.

Preferably $R^{B3}$ and/or $R^{B3SN}$ are each independently selected from chloro, fluoro, bromo, methyl, ethyl, difluoromethyl, trifluoromethyl $C_1$-$C_3$haloalkoxy, $C_1$-$C_3$alkoxy, or $C_1$-$C_3$alkyl. The skilled man will appreciate that where ring A is trisubstituted, $R^{B3}$ and $R^{B3SN}$ may be the same or different.

In compounds of formula (X) as defined herein, $R^{Q1}$ and $R^{Q4}$ are each hydrogen, and $R^{Q2}$ and $R^{Q3}$ together with the carbon atoms to which they are joined form ring Q, which is an optionally substituted 5-membered thio-lactam ring. In preferred embodiments Q has the structure Q1 or Q2, wherein 'a' denotes the point of attachment to ring A, and 'c' denotes the point of attachment to the carboxylate moiety

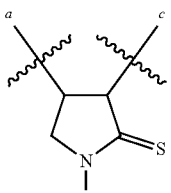
Q1

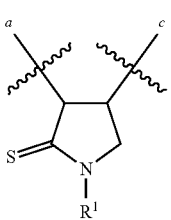
Q2

In preferred embodiments the Hal substituent in a compound of formula (A) is iodo or bromo.

Compounds of formula (X) may be used as intermediates in the manufacture of pharmaceuticals and agrochemicals comprising pyrazolo-pyrrolidone motifs. For example, US2007/0123508 describes 2-oxo-1-pyrrolidone derivatives for use as PAR2 inhibitors, compounds of formula (X) may be used in the synthesis of such compounds wherein $R^1$ of the compound of US2007/0123508 is a substituted pyrazole. US2004/0242671 describes 2-oxo-1-pyrrolidine derivatives for use as therapeutic agents to treat dyskinesia; compounds of formula (X) may be used to such compounds wherein $R^3$ of formula (II) of US2004/0242671 is a di-/tri-substituted pyrazole and $R^4$ is amido.

U.S. Pat. No. 4,874,422 describes 1-phenyl-3-carboxyamidopyrrolidones as herbicides, and compounds of formula (X) may be used in the manufacture of compounds of formula (I) as described therein, but wherein $R^3$ is a di-substituted pyrazole. The manufacture of novel herbicidal compounds using compounds of formula (X) is also described herein.

Thus, in further aspects, there is provided the use of a compound of formula (X) in the preparation of an agrochemical, in particular in the preparation of a herbicide, as well as the use of a compound of formula (X) in the preparation of a pharmaceutical, in particular a pharmaceutical for the prevention and/or treatment of diseases and disorders related to PAR2, and/or the treatment of dyskinesia.

Depending upon the desired ultimate end-product $R^1$ is selected from the group consisting of $C_1$-$C_6$ alkyl, $C_2$-$C_6$alkenyl, $C_3$-$C_6$cycloalkyl, $C_3$-$C_6$cycloalkenyl, optionally substituted phenyl, optionally substituted $C_5$-$C_6$ heteroaryl, —$CR^{12}R^{13}$, or —$C(O)R^{12}$; $R^{12}$ is hydrogen, OH, $C_1$-$C_3$ alkoxy, or $C_1$-$C_4$ alkyl. $R^{13}$ is —$C(O)NH_2$.

Where substituted, said phenyl or $C_5$-$C_6$ heteroaryl is preferably substituted by 1, 2 or 3 $R^{11}$ substituents.

Each $R^{11}$ is independently halogen, OH, $C_1$-$C_6$alkyl, $C_1$-$C_6$haloalkyl, $C_1$-$C_6$ alkoxy, $C_1$-$C_6$haloalkoxy, $C_1$-$C_3$alkoxy-$C_1$-$C_3$alkyl, $C_2$-$C_6$alkenyl, $C_2$-$C_6$alkynyl, nitro, cyano, or amino.

In one embodiment $R^1$ is 3-$CF_3$-phenyl-.

More preferably, $R^1$ is $C_1$-$C_3$alkyl, or —$CR^{12}R^{13}$. Preferably $R^{12}$ methyl or ethyl, more preferably ethyl. Most preferably $R^1$ is methyl.

Examples of suitable $R^2$ substituents include hydrogen, $C_1$-$C_6$alkyl, —$C_r$alkoxyC$_s$alkyl, $C_1$-$C_6$haloalkyl, —$C_r$alkoxyC$_s$haloalkyl, $C_2$-$C_6$alkenyl, $C_2$-$C_6$alkynyl, and —$(CR^{21}R^{22})_tR^{20}$ wherein each $R^{20}$ is independently —$C(O)OR^{23}$, —$OC(O)R^{23}$, —$C_3$-$C_6$cycloalkyl, or an -aryl, -aryloxy, -heteroaryl, -heteroaryloxy or -heterocyclyl ring, wherein said ring is optionally substituted by 1 to 3 independent $R^{25}$; r is an integer of 1, 2, 3, 4, or 5, s is an integer of 1, 2, 3, 4, or 5, and the sum of r+s is less than or equal to 6; t is an integer of 0, 1, 2, 3, 4, 5 or 6, each $R^{21}$ is independently hydrogen or $C_1$-$C_2$ alkyl; each $R^{22}$ is independently hydrogen or $C_1$-$C_2$ alkyl; $R^{23}$ is hydrogen or $C_1$-$C_4$alkyl.

In certain embodiments, where $R^2$ is an aryl or heteroaryl ring optionally substituted by 1 to 3 $R^{25}$, and said aryl or heteroaryl ring is selected from the group consisting of a phenyl, pyridinyl, and a thienyl ring system, it may be represented by the following generic structure

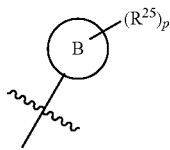

wherein ring B is a phenyl, pyridinyl, or thienyl ring, p is an integer or 0, 1, 2, or 3, and the jagged line represents the point of attachment of the ring to the rest of the molecule, in this case via the amide nitrogen.

In certain embodiments $R^2$ is selected from the group consisting of $R^2$-1, $R^2$-2, $R^2$-3, $R^2$-4, $R^2$-5, and $R^2$-6, wherein p and the jagged line are as described previously, and each $R^{25}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl

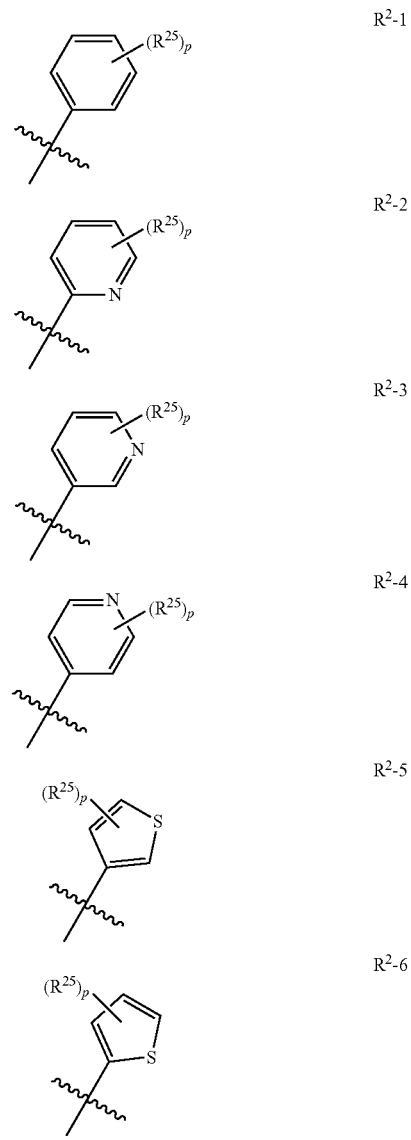

More preferably each $R^{25}$ is independently halogen, $C_1$-$C_4$ alkyl, $C_1$-$C_3$ haloalkyl, $C_1$-$C_3$alkoxy, or $C_1$-$C_3$haloalkoxy; even more preferably chloro, fluoro, bromo, $C_1$-$C_2$haloalkyl, $C_1$-$C_2$haloalkoxy, or $C_1$-$C_2$alkoxy; more preferably still fluoro, ethyl, trifluoromethyl, difluoroethyl, methoxy, difluoromethoxy, or trifluoromethoxy. As stated herein, the value of p is 1, 2 or 3. Preferably p is 0, 1, or 2 and each $R^{25}$ is borne by a ring carbon atom.

In one particular set of embodiments of compounds of formula (H) and formula (I) p is 2 and at least one $R^{25}$ is fluoro. Preferably p is 0, 1, or 2 and each $R^{25}$ is borne by a ring carbon atom.

As stated supra, compounds of formulae (B), (D), (E), (X), (H) and (I) are novel, as are compounds of formula (J), and these compounds all form yet further aspects on the invention. Tables 1 to 7 below, give specific examples of these compounds falling within the scope of the invention.

TABLE 1

Compounds of formula (B) for use as described herein

| Cmpd. No | Name | 1HNMR (CDCl$_3$) |
|---|---|---|
| 1.001 | ethyl (E)-3-[1-methyl-5-(trifluoromethyl)pyrazol-3-yl]prop-2-enoate | δ = 7.58 (d, J = 16.1 Hz, 1H), 6.81 (s, 1H), 6.43 (d, J = 16.1 Hz, 1H), 4.26 (q, J = 7.2 Hz, 2H), 4.00 (d, 3H), 1.33 (t, J = 7.1 Hz, 3H) |
| 1.002 | ethyl (E)-3-[1-methyl-5-(trifluoromethyl)pyrazol-4-yl]prop-2-enoate | |
| 1.003 | ethyl (E)-3-(5-chloro-1-methyl-pyrazol-3-yl)prop-2-enoate | δ = 7.54 (d, 1H), 6.43 (s, 1H), 6.34 (d, 1H), 4.25 (q, 2H), 3.86 (s, 3H), 1.32 (t, 3H) |
| 1.004 | ethyl (E)-3-(5-chloro-1-methyl-pyrazol-4-yl)prop-2-enoate | |
| 1.005 | ethyl (E)-3-(5-chloro-2-methyl-pyrazol-3-yl)prop-2-enoate | |
| 1.006 | ethyl (E)-3-(4-bromo-5-chloro-1-methyl-pyrazol-3-yl)prop-2-enoate | |
| 1.007 | ethyl (E)-3-(4-bromo-5-chloro-2-methyl-pyrazol-3-yl)prop-2-enoate | |
| 1.008 | ethyl (E)-3-(3-bromo-5-chloro-1-methyl-pyrazol-4-yl)prop-2-enoate | |

TABLE 2

Compounds of formula (D) for use as described herein

| Cmpd. No | Name | 1HNMR (CDCl$_3$) |
|---|---|---|
| 2.001 | ethyl 6-methyl-9-[1-methyl-5-(trifluoromethyl)pyrazol-3-yl]-1,4-dithia-6-azaspiro[4.4]nonane-8-carboxylate | δ = 6.78 (s, 1H), 4.25 (d, J = 9.5 Hz, 1H), 4.13 (q, J = 7.1 Hz, 2H), 3.96 (s, 3H), 3.47 (dt, J = 5.9, 9.8 Hz, 1H), 3.29-3.09 (m, 3H), 3.05-2.99 (m, 1H), 2.95 (t, 1H), 2.81 (ddd, J = 4.5, 7.0, 11.2 Hz, 1H), 2.46 (s, 3H), 1.21 (t, J = 7.2 Hz, 3H) |
| 2.002 | ethyl 6-methyl-9-[1-methyl-5-(trifluoromethyl)pyrazol-4-yl]-1,4-dithia-6-azaspiro[4.4]nonane-8-carboxylate | |
| 2.003 | ethyl 9-(5-chloro-1-methyl-pyrazol-3-yl)-6-methyl-1,4-dithia-6-azaspiro[4.4]nonane-8-carboxylate | δ = 6.37 (s, 1H), 4.22 (d, 1H), 4.13 (q, 2H), 3.81 (s, 3H), 3.48-3.38 (m, 1H), 3.26-3.01 (m, 4H), 2.99-2.83 (m, 2H), 2.46 (s, 3H), 1.21 (t, J = 7.2 Hz, 3H) |
| 2.004 | ethyl 9-(5-chloro-1-methyl-pyrazol-4-yl)-6-methyl-1,4-dithia-6-azaspiro[4.4]nonane-8-carboxylate | |
| 2.005 | ethyl 9-(5-chloro-2-methyl-pyrazol-3-yl)-6-methyl-1,4-dithia-6-azaspiro[4.4]nonane-8-carboxylate | |
| 2.006 | ethyl 9-(4-bromo-5-chloro-1-methyl-pyrazol-3-yl)-6-methyl-1,4-dithia-6-azaspiro[4.4]nonane-8-carboxylate | |
| 2.007 | ethyl 9-(4-bromo-5-chloro-2-methyl-pyrazol-3-yl)-6-methyl-1,4-dithia-6-azaspiro[4.4]nonane-8-carboxylate | |
| 2.008 | ethyl 9-(3-bromo-5-chloro-1-methyl-pyrazol-4-yl)-6-methyl-1,4-dithia-6-azaspiro[4.4]nonane-8-carboxylate | |

TABLE 3

Compounds of formula (E) for use as described herein

| Cmpd. No | Name | 1HNMR (CDCl$_3$) |
|---|---|---|
| 3.001 | ethyl 6-methyl-8-[1-methyl-5-(trifluoromethyl)pyrazol-3-yl]-1,4-dithia-6-azaspiro[4.4]nonane-9-carboxylate | δ = 6.45 (s, 1H), 4.32-4.16 (m, 2H), 3.90 (s, 3H), 3.89-3.78 (m, 2H), 3.32-3.09 (m, 5H), 2.97-2.90 (m, 1H), 2.47 (s, 3H), 1.31 (t, J = 7.2 Hz, 3H) |
| 3.002 | ethyl 6-methyl-8-[1-methyl-5-(trifluoromethyl)pyrazol-4-yl]-1,4-dithia-6-azaspiro[4.4]nonane-9-carboxylate | |

TABLE 3-continued

Compounds of formula (E) for use as described herein

| Cmpd. No | Name | 1HNMR (CDCl₃) |
|---|---|---|
| 3.003 | ethyl 8-(5-chloro-1-methyl-pyrazol-3-yl)-6-methyl-1,4-dithia-6-azaspiro[4.4]nonane-9-carboxylate | δ = 6.05 (s, 1H), 4.32-4.15 (m, 2H), 3.87-3.71 (m, 5H), 3.32-3.06 (m, 5H), 2.96-2.87 (m, 1H), 2.46 (s, 3H), 1.31 (t, J = 7.2 Hz, 3H) |
| 3.004 | ethyl 8-(5-chloro-1-methyl-pyrazol-4-yl)-6-methyl-1,4-dithia-6-azaspiro[4.4]nonane-9-carboxylate | |
| 3.005 | ethyl 8-(5-chloro-2-methyl-pyrazol-3-yl)-6-methyl-1,4-dithia-6-azaspiro[4.4]nonane-9-carboxylate | |
| 3.006 | ethyl 8-(4-bromo-5-chloro-1-methyl-pyrazol-3-yl)-6-methyl-1,4-dithia-6-azaspiro[4.4]nonane-9-carboxylate | |
| 3.007 | ethyl 8-(4-bromo-5-chloro-2-methyl-pyrazol-3-yl)-6-methyl-1,4-dithia-6-azaspiro[4.4]nonane-9-carboxylate | |
| 3.008 | ethyl 8-(3-bromo-5-chloro-1-methyl-pyrazol-4-yl)-6-methyl-1,4-dithia-6-azaspiro[4.4]nonane-9-carboxylate | |

TABLE 4

Compounds of formula (X) for use as described herein

| Cmpd. No | Name |
|---|---|
| 4.001 | 4-(3-bromo-5-chloro-1-methyl-pyrazol-4-yl)-2-thioxo-pyrrolidine-3-carboxylic acid |
| 4.002 | 1-methyl-4-[1-methyl-5-(trifluoromethyl)pyrazol-3-yl]-2-thioxo-pyrrolidine-3-carboxylic acid |
| 4.003 | 1-methyl-4-[1-methyl-5-(trifluoromethyl)pyrazol-4-yl]-2-thioxo-pyrrolidine-3-carboxylic acid |
| 4.004 | 4-(5-chloro-1-methyl-pyrazol-3-yl)-1-methyl-2-thioxo-pyrrolidine-3-carboxylic acid |
| 4.005 | 4-(5-chloro-1-methyl-pyrazol-4-yl)-1-methyl-2-thioxo-pyrrolidine-3-carboxylic acid |
| 4.006 | 4-(5-chloro-2-methyl-pyrazol-3-yl)-1-methyl-2-thioxo-pyrrolidine-3-carboxylic acid |
| 4.007 | 4-(4-bromo-5-chloro-1-methyl-pyrazol-3-yl)-1-methyl-2-thioxo-pyrrolidine-3-carboxylic acid |
| 4.008 | 4-(3-bromo-5-chloro-1-methyl-pyrazol-4-yl)-1-methyl-2-thioxo-pyrrolidine-3-carboxylic acid |

TABLE 5

Compounds of formula (H1) as described herein

| Compound No. | Name |
|---|---|
| 5.001 | (3S,4R)-N-(2,3-difluorophenyl)-1-methyl-4-[1-methyl-5-(trifluoromethyl)pyrazol-3-yl]-2-thioxo-pyrrolidine-3-carboxamide |
| 5.002 | (3S,4R)-N-(2-fluorophenyl)-1-methyl-4-[1-methyl-5-(trifluoromethyl)pyrazol-3-yl]-2-thioxo-pyrrolidine-3-carboxamide |
| 5.003 | (3S,4R)-N-(2,4-difluorophenyl)-1-methyl-4-[1-methyl-5-(trifluoromethyl)pyrazol-3-yl]-2-thioxo-pyrrolidine-3-carboxamide |
| 5.004 | (3S,4R)-N-[3-fluoro-2-(trifluoromethoxy)phenyl]-1-methyl-4-[1-methyl-5-(trifluoromethyl)pyrazol-3-yl]-2-thioxo-pyrrolidine-3-carboxamide |
| 5.005 | (3S,4R)-N-[3-fluoro-2-(trifluoromethyl)phenyl]-1-methyl-4-[1-methyl-5-(trifluoromethyl)pyrazol-3-yl]-2-thioxo-pyrrolidine-3-carboxamide |
| 5.006 | (3S,4R)-N-(3-fluoro-2-methoxy-phenyl)-1-methyl-4-[1-methyl-5-(trifluoromethyl)pyrazol-3-yl]-2-thioxo-pyrrolidine-3-carboxamide |
| 5.007 | (3S,4R)-1-methyl-4-[1-methyl-5-(trifluoromethyl)pyrazol-3-yl]-2-thioxo-N-(2,3,4-trifluorophenyl)pyrrolidine-3-carboxamide |
| 5.008 | (3S,4R)-N-(2,6-difluoro-3-pyridyl)-1-methyl-4-[1-methyl-5-(trifluoromethyl)pyrazol-3-yl]-2-thioxo-pyrrolidine-3-carboxamide |
| 5.009 | (3S,4R)-N-(6-fluoro-2-pyridyl)-1-methyl-4-[1-methyl-5-(trifluoromethyl)pyrazol-3-yl]-2-thioxo-pyrrolidine-3-carboxamide |
| 5.010 | (3S,4R)-N-[2-(difluoromethon)-3-fluoro-phenyl]-1-methyl-4-[1-methyl-5-(trifluoromethyl)pyrazol-3-yl]-2-thioxo-pyrrolidine-3-carboxamide |
| 5.011 | (3S,4R)-N-(2-ethylphenyl)-1-methyl-4-[1-methyl-5-(trifluoromethyl)pyrazol-3-yl]-2-thioxo-pyrrolidine-3-carboxamide |
| 5.012 | (3S,4R)-N-[2-(1,1-difluoroethyl)-3-fluoro-phenyl]-1-methyl-4-[1-methyl-5-(trifluoromethyl)pyrazol-3-yl]-2-thioxo-pyrrolidine-3-carboxamide |
| 5.013 | (3S,4R)-N-(2-chloro-3-thienyl)-1-methyl-4-[1-methyl-5-(trifluoromethyl)pyrazol-3-yl]-2-thioxo-pyrrolidine-3-carboxamide |
| 5.014 | (3S,4R)-N-(2-fluoro-3-thienyl)-1-methyl-4-[1-methyl-5-(trifluoromethyl)pyrazol-3-yl]-2-thioxo-pyrrolidine-3-carboxamide |

TABLE 5-continued

Compounds of formula (H1) as described herein

| Compound No. | Name |
|---|---|
| 5.015 | (3S,4S)-N-(2,3-difluorophenyl)-1-methyl-4-[1-methyl-5-(trifluoromethyl)pyrazol-4-yl]-2-thioxo-pyrrolidine-3-carboxamide |
| 5.016 | (3S,4S)-N-(2-fluorophenyl)-1-methyl-4-[1-methyl-5-(trifluoromethyl)pyrazol-4-yl]-2-thioxo-pyrrolidine-3-carboxamide |
| 5.017 | (3S,4S)-N-(2,4-difluorophenyl)-1-methyl-4-[1-methyl-5-(trifluoromethyl)pyrazol-4-yl]-2-thioxo-pyrrolidine-3-carboxamide |
| 5.018 | (3S,4S)-N-[3-fluoro-2-(trifluoromethyl)phenyl]-1-methyl-4-[1-methyl-5-(trifluoromethyl)pyrazol-4-yl]-2-thioxo-pyrrolidine-3-carboxamide |
| 5.019 | (3S,4S)-N-[3-fluoro-2-(trifluoromethyl)phenyl]-1-methyl-4-[1-methyl-5-(trifluoromethyl)pyrazol-4-yl]-2-thioxo-pyrrolidine-3-carboxamide |
| 5.020 | (3S,4S)-N-(3-fluoro-2-methoxy-phenyl)-1-methyl-4-[1-methyl-5-(trifluoromethyl)pyrazol-4-yl]-2-thioxo-pyrrolidine-3-carboxamide |
| 5.021 | (3S,4S)-1-methyl-4-[1-methyl-5-(trifluoromethyl)pyrazol-4-yl]-2-thioxo-N-(2,3,4-trifluorophenyl)pyrrolidine-3-carboxamide |
| 5.022 | (3S,4S)-N-(2,6-difluoro-3-pyridyl)-1-methyl-4-[1-methyl-5-(trifluoromethyl)pyrazol-4-yl]-2-thioxo-pyrrolidine-3-carboxamide |
| 5.023 | (3S,4S)-N-[2-(1,1-difluoroethyl)-3-fluoro-phenyl]-1-methyl-4-[1-methyl-5-(trifluoromethyl)pyrazol-4-yl]-2-thioxo-pyrrolidine-3-carboxamide |
| 5.024 | (3S,4S)-N-[2-(difluoromethoxy)-3-fluoro-phenyl]-1-methyl-4-[1-methyl-5-(trifluoromethyl)pyrazol-4-yl]-2-thioxo-pyrrolidine-3-carboxamide |
| 5.025 | (3S,4S)-N-[2-(difluoromethoxy)-3-fluoro-phenyl]-1-methyl-4-[1-methyl-5-(trifluoromethyl)pyrazol-4-yl]-2-thioxo-pyrrolidine-3-carboxamide |
| 5.026 | (3S,4S)-N-(2-ethylphenyl)-1-methyl-4-[1-methyl-5-(trifluoromethyl)pyrazol-4-yl]-2-thioxo-pyrrolidine-3-carboxamide |
| 5.027 | (3S,4R)-N-(2-chloro-3-thienyl)-1-methyl-4-[1-methyl-5-(trifluoromethyl)pyrazol-3-yl]-2-thioxo-pyrrolidine-3-carboxamide |
| 5.028 | (3S,4S)-N-(2-fluoro-3-thienyl)-1-methyl-4-[1-methyl-5-(trifluoromethyl)pyrazol-4-yl]-2-thioxo-pyrrolidine-3-carboxamide |
| 5.029 | (3S,4R)-N-(2,3-difluorophenyl)-1-methyl-4-[2-methyl-5-(trifluoromethyl)pyrazol-3-yl]-2-thioxo-pyrrolidine-3-carboxamide |
| 5.030 | (3S)-N-(2-fluorophenyl)-1-methyl-4-[2-methyl-5-(trifluoromethyl)pyrazol-3-yl]-2-thioxo-pyrrolidine-3-carboxamide |
| 5.031 | (3S,4R)-N-(2,4-difluorophenyl)-1-methyl-4-[2-methyl-5-(trifluoromethyl)pyrazol-3-yl]-2-thioxo-pyrrolidine-3-carboxamide |
| 5.032 | (3S,4R)-N-[3-fluoro-2-(trifluoromethoxy)phenyl]-1-methyl-4-[2-methyl-5-(trifluoromethyl)pyrazol-3-yl]-2-thioxo-pyrrolidine-3-carboxamide |
| 5.033 | (3S,4R)-N-[3-fluoro-2-(trifluoromethyl)phenyl]-1-methyl-4-[2-methyl-5-(trifluoromethyl)pyrazol-3-yl]-2-thioxo-pyrrolidine-3-carboxamide |
| 5.034 | (3S,4R)-N-(3-fluoro-2-methoxy-phenyl)-1-methyl-4-[2-methyl-5-(trifluoromethyl)pyrazol-3-yl]-2-thioxo-pyrrolidine-3-carboxamide |
| 5.035 | (3S,4R)-1-methyl-4-[2-methyl-5-(trifluoromethyl)pyrazol-3-yl]-2-thioxo-N-(2,3,4-trifluorophenyl)pyrrolidine-3-carboxamide |
| 5.036 | (3S,4R)-N-(2,6-difluoro-3-pyridyl)-1-methyl-4-[1-methyl-3-(trifluoromethyl)-3H-pyrazol-5-yl]-2-thioxo-pyrrolidine-3-carboxamide |
| 5.037 | (3S,4R)-N-(6-fluoro-2-pyridyl)-1-methyl-4-[1-methyl-3-(trifluoromethyl)-3H-pyrazol-5-yl]-2-thioxo-pyrrolidine-3-carboxamide |
| 5.038 | (3S,4R)-N-[2-(difluoromethoxy)-3-fluoro-phenyl]-1-methyl-4-[1-methyl-3-(trifluoromethyl)-3H-pyrazol-5-yl]-2-thioxo-pyrrolidine-3-carboxamide |
| 5.039 | (3S,4R)-N-(2-ethylphenyl)-1-methyl-4-[1-methyl-3-(trifluoromethyl)-3H-pyrazol-5-yl]-2-thioxo-pyrrolidine-3-carboxamide |
| 5.040 | (3S,4R)-N-[2-(1,1-difluoroethyl)-3-fluoro-phenyl]-1-methyl-4-[1-methyl-3-(trifluoromethyl)-3H-pyrazol-5-yl]-2-thioxo-pyrrolidine-3-carboxamide |
| 5.041 | (3S,4R)-N-(2-chloro-3-thienyl)-1-methyl-4-[1-methyl-3-(trifluoromethyl)-3H-pyrazol-5-yl]-2-thioxo-pyrrolidine-3-carboxamide |
| 5.042 | (3S,4R)-N-(2-fluoro-3-thienyl)-1-methyl-4-[1-methyl-3-(trifluoromethyl)-3H-pyrazol-5-yl]-2-thioxo-pyrrolidine-3-carboxamide |
| 5.043 | (3S,4R)-4-(5-chloro-1-methyl-pyrazol-3-yl)-N-(2,3-difluorophenyl)-1-methyl-2-thioxo-pyrrolidine-3-carboxamide |
| 5.044 | (3S,4R)-4-(5-chloro-1-methyl-pyrazol-3-yl)-N-(2-fluorophenyl)-1-methyl-2-thioxo-pyrrolidine-3-carboxamide |
| 5.045 | (3S,4R)-4-(5-chloro-1-methyl-pyrazol-3-yl)-N-(2,4-difluorophenyl)-1-methyl-2-thioxo-pyrrolidine-3-carboxamide |
| 5.046 | (3S,4R)-4-(5-chloro-1-methyl-pyrazol-3-yl)-N-[3-fluoro-2-(trifluoromethoxy)phenyl]-1-methyl-2-thioxo-pyrrolidine-3-carboxamide |
| 5.047 | (3S,4R)-4-(5-chloro-1-methyl-pyrazol-3-yl)-N-[3-fluoro-2-(trifluoromethyl)phenyl]-1-methyl-2-thioxo-pyrrolidine-3-carboxamide |
| 5.048 | (3S,4R)-4-(5-chloro-1-methyl-pyrazol-3-yl)-N-(3-fluoro-2-methoxy-phenyl)-1-methyl-2-thioxo-pyrrolidine-3-carboxamide |
| 5.049 | (3S,4R)-4-(5-chloro-1-methyl-pyrazol-3-yl)-1-methyl-2-thioxo-N-(2,3,4-trifluorophenyl)pyrrolidine-3-carboxamide |
| 5.050 | (3S,4R)-4-(5-chloro-1-methyl-pyrazol-3-yl)-N-(2,6-difluoro-3-pyridyl)-1-methyl-2-thioxo-pyrrolidine-3-carboxamide |
| 5.051 | (3S,4R)-4-(5-chloro-1-methyl-pyrazol-3-yl)-N-(6-fluoro-2-pyridyl)-1-methyl-2-thioxo-pyrrolidine-3-carboxamide |

TABLE 5-continued

Compounds of formula (H1) as described herein

| Compound No. | Name |
| --- | --- |
| 5.052 | (3S,4R)-4-(5-chloro-1-methyl-pyrazol-3-yl)-N-[2-(difluoromethoxy)-3-fluoro-phenyl]-1-methyl-2-thioxo-pyrrolidine-3-carboxamide |
| 5.053 | (3S,4R)-4-(5-chloro-1-methyl-pyrazol-3-yl)-N-(2-ethylphenyl)-1-methyl-2-thioxo-pyrrolidine-3-carboxamide |
| 5.054 | (3S,4R)-4-(4-bromo-5-chloro-1-methyl-pyrazol-3-yl)-N-[2-(1,1-difluoroethyl)-3-fluoro-phenyl]-1-methyl-2-thioxo-pyrrolidine-3-carboxamide |
| 5.055 | (3S,4R)-4-(5-chloro-1-methyl-pyrazol-3-yl)-N-(2-chloro-3-thienyl)-1-methyl-2-thioxo-pyrrolidine-3-carboxamide |
| 5.056 | (3S,4R)-4-(5-chloro-1-methyl-pyrazol-3-yl)-N-(2-fluoro-3-thienyl)-1-methyl-2-thioxo-pyrrolidine-3-carboxamide |
| 5.057 | (3S,4S)-4-(5-chloro-1-methyl-pyrazol-4-yl)-N-(2,3-difluorophenyl)-1-methyl-2-thioxo-pyrrolidine-3-carboxamide |
| 5.058 | (3S,4S)-4-(5-chloro-1-methyl-pyrazol-4-yl)-N-(2-fluorophenyl)-1-methyl-2-thioxo-pyrrolidine-3-carboxamide |
| 5.059 | (3S,4S)-4-(5-chloro-1-methyl-pyrazol-4-yl)-N-(2,4-difluorophenyl)-1-methyl-2-oxo-pyrrolidine-3-carboxamide |
| 5.060 | (3S,4S)-4-(5-chloro-1-methyl-pyrazol-4-yl)-N-[3-fluoro-2-(trifluoromethoxy)phenyl]-1-methyl-2-thioxo-pyrrolidine-3-carboxamide |
| 5.061 | (3S,4S)-4-(5-chloro-1-methyl-pyrazol-4-yl)-N-[3-fluoro-2-(trifluoromethyl)phenyl]-1-methyl-2-thioxo-pyrrolidine-3-carboxamide |
| 5.062 | (3S,4S)-4-(5-chloro-1-methyl-pyrazol-4-yl)-N-(3-fluoro-2-methoxy-phenyl)-1-methyl-2-thioxo-pyrrolidine-3-carboxamide |
| 5.063 | (3S,4S)-4-(5-chloro-1-methyl-pyrazol-4-yl)-1-methyl-2-thioxo-N-(2,3,4-trifluorophenyl)pyrrolidine-3-carboxamide |
| 5.064 | (3S,4S)-4-(3-bromo-5-chloro-1-methyl-pyrazol-4-yl)-N-(2,6-difluoro-3-pyridyl)-1-methyl-2-thioxo-pyrrolidine-3-carboxamide |
| 5.065 | (3S,4S)-4-(5-chloro-1-methyl-pyrazol-4-yl)-N-(6-fluoro-2-pyridyl)-1-methyl-2-thioxo-pyrrolidine-3-carboxamide |
| 5.066 | (3S,4S)-4-(5-chloro-1-methyl-pyrazol-4-yl)-N-[2-(difluoromethoxy)-3-fluoro-phenyl]-1-methyl-2-thioxo-pyrrolidine-3-carboxamide |
| 5.067 | (3S,4S)-4-(5-chloro-1-methyl-pyrazol-4-yl)-N-(2-ethylphenyl)-1-methyl-2-thioxo-pyrrolidine-3-carboxamide |
| 5.068 | (3S,4S)-4-(5-chloro-1-methyl-pyrazol-4-yl)-N-[2-(1,1-difluoroethyl)-3-fluoro-phenyl]-1-methyl-2-thioxo-pyrrolidine-3-carboxamide |
| 5.069 | (3S,4S)-4-(5-chloro-1-methyl-pyrazol-4-yl)-N-(2-chloro-3-thienyl)-1-methyl-2-thioxo-pyrrolidine-3-carboxamide |
| 5.070 | (3S,4S)-4-(5-chloro-1-methyl-pyrazol-4-yl)-N-(2-fluoro-3-thienyl)-1-methyl-2-thioxo-pyrrolidine-3-carboxamide |
| 5.071 | (3S,4R)-4-(5-chloro-2-methyl-pyrazol-3-yl)-N-(2,3-difluorophenyl)-1-methyl-2-thioxo-pyrrolidine-3-carboxamide |
| 5.072 | (3S)-4-(5-chloro-2-methyl-pyrazol-3-yl)-N-(2-fluorophenyl)-1-methyl-2-oxo-pyrrolidine-3-carboxamide |
| 5.073 | (3S,4R)-4-(5-chloro-2-methyl-pyrazol-3-yl)-N-(2,4-difluorophenyl)-1-methyl-2-thioxo-pyrrolidine-3-carboxamide |
| 5.074 | (3S,4R)-4-(5-chloro-2-methyl-pyrazol-3-yl)-N-[3-fluoro-2-(trifluoromethoxy)phenyl]-1-methyl-2-thioxo-pyrrolidine-3-carboxamide |
| 5.075 | (3S,4R)-4-(5-chloro-2-methyl-pyrazol-3-yl)-N-[3-fluoro-2-(trifluoromethyl)phenyl]-1-methyl-2-thioxo-pyrrolidine-3-carboxamide |
| 5.076 | (3S,4R)-4-(5-chloro-2-methyl-pyrazol-3-yl)-N-(3-fluoro-2-methoxy-phenyl)-1-methyl-2-thioxo-pyrrolidine-3-carboxamide |
| 5.077 | (3S,4R)-1-methyl-4-[2-methyl-5-(trifluoromethyl)pyrazol-3-yl]-2-thioxo-N-(2,3,4-trifluorophenyl)pyrrolidine-3-carboxamide |
| 5.078 | (3S,4R)-N-(2,6-difluoro-3-pyridyl)-1-methyl-4-[1-methyl-3-(chorol)-3H-pyrazol-5-yl]-2-thioxo-pyrrolidine-3-carboxamide |
| 5.079 | (3S,4R)-N-(6-fluoro-2-pyridyl)-1-methyl-4-[1-methyl-3-(chloro)-3H-pyrazol-5-yl]-2-thioxo-pyrrolidine-3-carboxamide |
| 5.080 | (3S,4R)-N-[2-(difluoromethoxy)-3-fluoro-phenyl]-1-methyl-4-[1-methyl-3-(chloro)-3H-pyrazol-5-yl]-2-thioxo-pyrrolidine-3-carboxamide |
| 5.081 | (3S,4R)-N-(2-ethylphenyl)-1-methyl-4-[1-methyl-3-(chloro)-3H-pyrazol-5-yl]-2-thioxo-pyrrolidine-3-carboxamide |
| 5.082 | (3S,4R)-N-[2-(1,1-difluoroethyl)-3-fluoro-phenyl]-1-methyl-4-[1-methyl-3-(chloro)-3H-pyrazol-5-yl]-2-thioxo-pyrrolidine-3-carboxamide |
| 5.083 | (3S,4R)-N-(2-chloro-3-thienyl)-1-methyl-4-[1-methyl-3-(chloro)-3H-pyrazol-5-yl]-2-thioxo-pyrrolidine-3-carboxamide |
| 5.084 | (3S,4R)-N-(2-fluoro-3-thienyl)-1-methyl-4-[1-methyl-3-(chloro)-3H-pyrazol-5-yl]-2-thioxo-pyrrolidine-3-carboxamide |
| 5.085 | (3S,4R)-4-(4-bromo-5-chloro-1-methyl-pyrazol-3-yl)-N-(2,3-difluorophenyl)-1-methyl-2-thioxo-pyrrolidine-3-carboxamide |
| 5.086 | (3S,4R)-4-(4-bromo-5-chloro-1-methyl-pyrazol-3-yl)-N-(2-fluorophenyl)-1-methyl-2-thioxo-pyrrolidine-3-carboxamide |
| 5.087 | (3S,4R)-4-(4-bromo-5-chloro-1-methyl-pyrazol-3-yl)-N-(2,4-difluorophenyl)-1-methyl-2-thioxo-pyrrolidine-3-carboxamide |
| 5.088 | (3S,4R)-4-(4-bromo-5-chloro-1-methyl-pyrazol-3-yl)-N-[3-fluoro-2-(trifluoromethoxy)phenyl]-1-methyl-2-thioxo-pyrrolidine-3-carboxamide |

TABLE 5-continued

Compounds of formula (H1) as described herein

| Compound No. | Name |
|---|---|
| 5.089 | (3S,4R)-4-(4-bromo-5-chloro-1-methyl-pyrazol-3-yl)-N-[3-fluoro-2-(trifluoromethyl)phenyl]-1-methyl-2-thioxo-pyrrolidine-3-carboxamide |
| 5.090 | (3S,4R)-4-(4-bromo-5-chloro-1-methyl-pyrazol-3-yl)-N-(3-fluoro-2-methoxy-phenyl)-1-methyl-2-thioxo-pyrrolidine-3-carboxamide |
| 5.091 | (3S,4R)-4-(4-bromo-5-chloro-1-methyl-pyrazol-3-yl)-1-methyl-2-thioxo-N-(2,3,4-trifluorophenyl)pyrrolidine-3-carboxamide |
| 5.092 | (3S,4R)-4-(4-bromo-5-chloro-1-methyl-pyrazol-3-yl)-N-(2,6-difluoro-3-pyridyl)-1-methyl-2-thioxo-pyrrolidine-3-carboxamide |
| 5.093 | (3S,4R)-4-(4-bromo-5-chloro-1-methyl-pyrazol-3-yl)-N-(6-fluoro-2-pyridyl)-1-methyl-2-thioxo-pyrrolidine-3-carboxamide |
| 5.094 | (3S,4R)-4-(4-bromo-5-chloro-1-methyl-pyrazol-3-yl)-N-[2-(difluoromethoxy)-3-fluoro-phenyl]-1-methyl-2-thioxo-pyrrolidine-3-carboxamide |
| 5.095 | (3S,4R)-4-(4-bromo-5-chloro-1-methyl-pyrazol-3-yl)-N-(2-ethylphenyl)-1-methyl-2-thioxo-pyrrolidine-3-carboxamide |
| 5.096 | (3S,4R)-4-(4-bromo-5-chloro-1-methyl-pyrazol-3-yl)-N-[2-(1,1-difluoroethyl)-3-fluoro-phenyl]-1-methyl-2-thioxo-pyrrolidine-3-carboxamide |
| 5.097 | (3S,4R)-4-(4-bromo-5-chloro-1-methyl-pyrazol-3-yl)-N-(2-chloro-3-thienyl)-1-methyl-2-thioxo-pyrrolidine-3-carboxamide |
| 5.098 | (3S,4R)-4-(4-bromo-5-chloro-1-methyl-pyrazol-3-yl)-N-(2-fluoro-3-thienyl)-1-methyl-2-thioxo-pyrrolidine-3-carboxamide |
| 5.099 | (3S,4S)-4-(3-bromo-5-chloro-1-methyl-pyrazol-4-yl)-N-(2,3-difluorophenyl)-1-methyl-2-thioxo-pyrrolidine-3-carboxamide |
| 5.100 | (3S,4S)-4-(3-bromo-5-chloro-1-methyl-pyrazol-4-yl)-N-(2-fluorophenyl)-1-methyl-2-thioxo-pyrrolidine-3-carboxamide |
| 5.101 | (3S,4S)-4-(3-bromo-5-chloro-1-methyl-pyrazol-4-yl)-N-(2,4-difluorophenyl)-1-methyl-2-thioxo-pyrrolidine-3-carboxamide |
| 5.102 | (3S,4S)-4-(3-bromo-5-chloro-1-methyl-pyrazol-4-yl)-N-3-fluoro-2-(trifluoromethoxy)phenyl]-1-methyl-2-thioxo-pyrrolidine-3-carboxamide |
| 5.103 | (3S,4S)-4-(3-bromo-5-chloro-1-methyl-pyrazol-4-yl)-N-[3-fluoro-2-(trifluoromethyl)phenyl]-1-methyl-2-thioxo-pyrrolidine-3-carboxamide |
| 5.104 | (3S,4S)-4-(3-bromo-5-chloro-1-methyl-pyrazol-4-yl)-N-(3-fluoro-2-methoxy-phenyl)-1-methyl-2-thioxo-pyrrolidine-3-carboxamide |
| 5.105 | (3S,4S)-4-(3-bromo-5-chloro-1-methyl-pyrazol-4-yl)-1-methyl-2-thioxo-N-(2,3,4-trifluorophenyl)pyrrolidine-3-carboxamide |
| 5.106 | (3S,4S)-4-(3-bromo-5-chloro-1-methyl-pyrazol-4-yl)-N-(2,6-difluoro-3-pyridyl)-1-methyl-2-thioxo-pyrrolidine-3-carboxamide |
| 5.107 | (3S,4S)-4-(3-bromo-5-chloro-1-methyl-pyrazol-4-yl)-N-(6-fluoro-2-pyridyl)-1-methyl-2-thioxo-pyrrolidine-3-carboxamide |
| 5.108 | (3S,4S)-4-(3-bromo-5-chloro-1-methyl-pyrazol-4-yl)-N-[2-(difluoromethoxy)-3-fluoro-phenyl]-1-methyl-2-thioxo-pyrrolidine-3-carboxamide |
| 5.109 | (3S,4S)-4-(3-bromo-5-chloro-1-methyl-pyrazol-4-yl)-N-(2-ethylphenyl)-1-methyl-2-thioxo-pyrrolidine-3-carboxamide |
| 5.110 | (3S,4S)-4-(3-bromo-5-chloro-1-methyl-pyrazol-4-yl)-N-[2-(1,1-difluoroethyl)-3-fluoro-phenyl]-1-methyl-2-thioxo-pyrrolidine-3-carboxamide |
| 5.111 | (3S,4S)-4-(3-bromo-5-chloro-1-methyl-pyrazol-4-yl)-N-(2-chloro-3-thienyl)-1-methyl-2-thioxo-pyrrolidine-3-carboxamide |
| 5.112 | (3S,4S)-4-(3-bromo-5-chloro-1-methyl-pyrazol-4-yl)-N-(2-fluoro-3-thienyl)-1-methyl-2-thioxo-pyrrolidine-3-carboxamide |
| 5.113 | (3S,4R)-4-(4-bromo-5-chloro-2-methyl-pyrazol-3-yl)-N-(2,3-difluorophenyl)-1-methyl-2-thioxo-pyrrolidine-3-carboxamide |
| 5.114 | (3S)-4-(4-bromo-5-chloro-2-methyl-pyrazol-3-yl)-N-(2-fluorophenyl)-1-methyl-2-thioxo-pyrrolidine-3-carboxamide |
| 5.115 | (3S,4R)-4-(4-bromo-5-chloro-2-methyl-pyrazol-3-yl)-N-(2,4-difluorophenyl)-1-methyl-2-thioxo-pyrrolidine-3-carboxamide |
| 5.116 | (3S,4R)-4-(4-bromo-5-chloro-2-methyl-pyrazol-3-yl)-N-[3-fluoro-2-(trifluoromethoxy)phenyl]-1-methyl-2-thioxo-pyrrolidine-3-carboxamide |
| 5.117 | (3S,4R)-4-(4-bromo-5-chloro-2-methyl-pyrazol-3-yl)-N-[3-fluoro-2-(trifluoromethyl)phenyl]-1-methyl-2-thioxo-pyrrolidine-3-carboxamide |
| 5.118 | (3S,4R)-4-(4-bromo-5-chloro-2-methyl-pyrazol-3-yl)-N-(3-fluoro-2-methoxy-phenyl)-1-methyl-2-thioxo-pyrrolidine-3-carboxamide |
| 5.119 | (3S,4R)-4-(4-bromo-5-chloro-2-methyl-pyrazol-3-yl)-1-methyl-2-thioxo-N-(2,3,4-trifluorophenyl)pyrrolidine-3-carboxamide |
| 5.120 | (3S,4R)-4-(4-bromo-3-chloro-1-methyl-3H-pyrazol-5-yl)-N-(2,6-difluoro-3-pyridyl)-1-methyl-2-thioxo-pyrrolidine-3-carboxamide |
| 5.121 | (3S,4R)-4-(4-bromo-3-chloro-1-methyl-3H-pyrazol-5-yl)-N-(6-fluoro-2-pyridyl)-1-methyl-2-thioxo-pyrrolidine-3-carboxamide |
| 5.122 | (3S,4R)-4-(4-bromo-3-chloro-1-methyl-3H-pyrazol-5-yl)-N-[2-(difluoromethoxy)-3-fluoro-phenyl]-1-methyl-2-thioxo-pyrrolidine-3-carboxamide |
| 5.123 | (3S,4R)-4-(4-bromo-3-chloro-1-methyl-3H-pyrazol-5-yl)-N-(2-ethylphenyl)-1-methyl-2-thioxo-pyrrolidine-3-carboxamide |
| 5.124 | (3S,4R)-4-(4-bromo-3-chloro-1-methyl-3H-pyrazol-5-yl)-N-[2-(1,1-difluoroethyl)-3-fluoro-phenyl]-1-methyl-2-thioxo-pyrrolidine-3-carboxamide |
| 5.125 | (3S,4R)-4-(4-bromo-3-chloro-1-methyl-3H-pyrazol-5-yl)-N-(2-chloro-3-thienyl)-1-methyl-2-thioxo-pyrrolidine-3-carboxamide |

TABLE 5-continued

Compounds of formula (H1) as described herein

| Compound No. | Name |
|---|---|
| 5.126 | (3S,4R)-4-(4-bromo-3-chloro-1-methyl-3H-pyrazol-5-yl)-N-(2-fluoro-3-thienyl)-1-methyl-2-thioxo-pyrrolidine-3-carboxamide |

TABLE 6

Compounds of formula (I1) as described herein

| Compound No. | Name |
|---|---|
| 6.001 | (3S,4R)-N-(2,3-difluorophenyl)-1-methyl-4-[1-methyl-5-(trifluoromethyl)pyrazol-3-yl]-2-oxo-pyrrolidine-3-carboxamide |
| 6.002 | (3S,4R)-N-(2-fluorophenyl)-1-methyl-4-[1-methyl-5-(trifluoromethyl)pyrazol-3-yl]-2-oxo-pyrrolidine-3-carboxamide |
| 6.003 | (3S,4R)-N-(2,4-difluorophenyl)-1-methyl-4-[1-methyl-5-(trifluoromethyl)pyrazol-3-yl]-2-oxo-pyrrolidine-3-carboxamide |
| 6.004 | (3S,4R)-N-[3-fluoro-2-(trifluoromethoxy)phenyl]-1-methyl-4-[1-methyl-5-(trifluoromethyl)pyrazol-3-yl]-2-oxo-pyrrolidine-3-carboxamide |
| 6.005 | (3S,4R)-N-[3-fluoro-2-(trifluoromethyl)phenyl]-1-methyl-4-[1-methyl-5-(trifluoromethyl)pyrazol-3-yl]-2-oxo-pyrrolidine-3-carboxamide |
| 6.006 | (3S,4R)-N-(3-fluoro-2-methoxy-phenyl)-1-methyl-4-[1-methyl-5-(trifluoromethyl)pyrazol-3-yl]-2-oxo-pyrrolidine-3-carboxamide |
| 6.007 | (3S,4R)-1-methyl-4-[1-methyl-5-(trifluoromethyl)pyrazol-3-yl]-2-oxo-N-(2,3,4-trifluorophenyl)pyrrolidine-3-carboxamide |
| 6.008 | (3S,4R)-N-(2,6-difluoro-3-pyridyl)-1-methyl-4-[1-methyl-5-(trifluoromethyl)pyrazol-3-yl]-2-oxo-pyrrolidine-3-carboxamide |
| 6.009 | (3S,4R)-N-(6-fluoro-2-pyridyl)-1-methyl-4-[1-methyl-5-(trifluoromethyl)pyrazol-3-yl]-2-oxo-pyrrolidine-3-carboxamide |
| 6.010 | (3S,4R)-N-[2-(difluoromethoxy)-3-fluoro-phenyl]-1-methyl-4-[1-methyl-5-(trifluoromethyl)pyrazol-3-yl]-2-oxo-pyrrolidine-3-carboxamide |
| 6.011 | (3S,4R)-N-(2-ethylphenyl)-1-methyl-4-[1-methyl-5-(trifluoromethyl)pyrazol-3-yl]-2-oxo-pyrrolidine-3-carboxamide |
| 6.012 | (3S,4R)-N-[2-(1,1-difluoroethyl)-3-fluoro-phenyl]-1-methyl-4-[1-methyl-5-(trifluoromethyl)pyrazol-3-yl]-2-oxo-pyrrolidine-3-carboxamide |
| 6.013 | (3S,4R)-N-(2-chloro-3-thienyl)-1-methyl-4-[1-methyl-5-(trifluoromethyl)pyrazol-3-yl]-2-oxo-pyrrolidine-3-carboxamide |
| 6.014 | (3S,4R)-N-(2-fluoro-3-thienyl)-1-methyl-4-[1-methyl-5-(trifluoromethyl)pyrazol-3-yl]-2-oxo-pyrrolidine-3-carboxamide |
| 6.015 | (3S,4S)-N-(2,3-difluorophenyl)-1-methyl-4-[1-methyl-5-(trifluoromethyl)pyrazol-4-yl]-2-oxo-pyrrolidine-3-carboxamide |
| 6.016 | (3S,4S)-N-(2-fluorophenyl)-1-methyl-4-[1-methyl-5-(trifluoromethyl)pyrazol-4-yl]-2-oxo-pyrrolidine-3-carboxamide |
| 6.017 | (3S,4S)-N-(2,4-difluorophenyl)-1-methyl-4-[1-methyl-5-(trifluoromethyl)pyrazol-4-yl]-2-oxo-pyrrolidine-3-carboxamid |
| 6.018 | (3S,4S)-N-[3-fluoro-2-(trifluoromethyl)phenyl]-1-methyl-4-[1-methyl-5-(trifluoromethyl)pyrazol-4-yl]-2-oxo-pyrrolidine-3-carboxamide |
| 6.019 | (3S,4S)-N-[3-fluoro-2-(trifluoromethyl)phenyl]-1-methyl-4-[1-methyl-5-(trifluoromethyl)pyrazol-4-yl]-2-oxo-pyrrolidine-3-carboxamide |
| 6.020 | (3S,4S)-N-(3-fluoro-2-methoxy-phenyl)-1-methyl-4-[1-methyl-5-(trifluoromethyl)pyrazol-4-yl]-2-oxo-pyrrolidine-3-carboxamide |
| 6.021 | (3S,4S)-1-methyl-4-[1-methyl-5-(trifluoromethyl)pyrazol-4-yl]-2-oxo-N-(2,3,4-trifluorophenyl)pyrrolidine-3-carboxamide |
| 6.022 | (3S,4S)-N-(2,6-difluoro-3-pyridyl)-1-methyl-4-[1-methyl-5-(trifluoromethyl)pyrazol-4-yl]-2-oxo-pyrrolidine-3-carboxamide |
| 6.023 | (3S,4S)-N-[2-(1,1-difluoroethyl)-3-fluoro-phenyl]-1-methyl-4-[1-methyl-5-(trifluoromethyl)pyrazol-4-yl]-2-oxo-pyrrolidine-3-carboxamide |
| 6.024 | (3S,4S)-N-[2-(difluoromethoxy)-3-fluoro-phenyl]-1-methyl-4-[1-methyl-5-(trifluoromethyl)pyrazol-4-yl]-2-oxo-pyrrolidine-3-carboxamide |
| 6.025 | (3S,4S)-N-[2-(difluoromethoxy)-3-fluoro-phenyl]-1-methyl-4-[1-methyl-5-(trifluoromethyl)pyrazol-4-yl]-2-oxo-pyrrolidine-3-carboxamide |
| 6.026 | (3S,4S)-N-(2-ethylphenyl)-1-methyl-4-[1-methyl-5-(trifluoromethyl)pyrazol-4-yl]-2-oxo-pyrrolidine-3-carboxamide |
| 6.027 | (3S,4R)-N-(2-chloro-3-thienyl)-1-methyl-4-[1-methyl-5-(trifluoromethyl)pyrazol-4-yl]-2-oxo-pyrrolidine-3-carboxamide |
| 6.028 | (3S,4S)-N-(2-fluoro-3-thienyl)-1-methyl-4-[1-methyl-5-(trifluoromethyl)pyrazol-4-yl]-2-oxo-pyrrolidine-3-carboxamide |
| 6.029 | (3S,4R)-N-(2,3-difluorophenyl)-1-methyl-4-[2-methyl-5-(trifluoromethyl)pyrazol-3-yl]-2-oxo-pyrrolidine-3-carboxamide |
| 6.030 | (3S)-N-(2-fluorophenyl)-1-methyl-4-[2-methyl-5-(trifluoromethyl)pyrazol-3-yl]-2-oxo-pyrrolidine-3-carboxamide |
| 6.031 | (3S,4R)-N-(2,4-difluorophenyl)-1-methyl-4-[2-methyl-5-(trifluoromethyl)pyrazol-3-yl]-2-oxo-pyrrolidine-3-carboxamide |

TABLE 6-continued

Compounds of formula (I1) as described herein

| Compound No. | Name |
|---|---|
| 6.032 | (3S,4R)-N-[3-fluoro-2-(trifluoromethoxy)phenyl]-1-methyl-4-[2-methyl-5-(trifluoromethyl)pyrazol-3-yl]-2-oxo-pyrrolidine-3-carboxamide |
| 6.033 | (3S,4R)-N-[3-fluoro-2-(trifluoromethyl)phenyl]-1-methyl-4-[2-methyl-5-(trifluoromethyl)pyrazol-3-yl]-2-oxo-pyrrolidine-3-carboxamide |
| 6.034 | (3S,4R)-N-(3-fluoro-2-methoxy-phenyl)-1-methyl-4-[2-methyl-5-(trifluoromethyl)pyrazol-3-yl]-2-oxo-pyrrolidine-3-carboxamide |
| 6.035 | (3S,4R)-1-methyl-4-[2-methyl-5-(trifluoromethyl)pyrazol-3-yl]-2-oxo-N-(2,3,4-trifluorophenyl)pyrrolidine-3-carboxamide |
| 6.036 | (3S,4R)-N-(2,6-difluoro-3-pyridyl)-1-methyl-4-[1-methyl-3-(trifluoromethyl)-3H-pyrazol-5-yl]-2-oxo-pyrrolidine-3-carboxamide |
| 6.037 | (3S,4R)-N-(6-fluoro-2-pyridyl)-1-methyl-4-[1-methyl-3-(trifluoromethyl)-3H-pyrazol-5-yl]-2-oxo-pyrrolidine-3-carboxamide |
| 6.038 | (3S,4R)-N-[2-(difluoromethoxy)-3-fluoro-phenyl]-1-methyl-4-[1-methyl-3-(trifluoromethyl)-3H-pyrazol-5-yl]-2-oxo-pyrrolidine-3-carboxamide |
| 6.039 | (3S,4R)-N-(2-ethylphenyl)-1-methyl-4-[1-methyl-3-(trifluoromethyl)-3H-pyrazol-5-yl]-2-oxo-pyrrolidine-3-carboxamide |
| 6.040 | (3S,4R)-N-[2-(1,1-difluoroethyl)-3-fluoro-phenyl]-1-methyl-4-[1-methyl-3-(trifluoromethyl)-3H-pyrazol-5-yl]-2-oxo-pyrrolidine-3-carboxamide |
| 6.041 | (3S,4R)-N-(2-chloro-3-thienyl)-1-methyl-4-[1-methyl-3-(trifluoromethyl)-3H-pyrazol-5-yl]-2-oxo-pyrrolidine-3-carboxamide |
| 6.042 | (3S,4R)-N-(2-fluoro-3-thienyl)-1-methyl-4-[1-methyl-3-(trifluoromethyl)-3H-pyrazol-5-yl]-2-oxo-pyrrolidine-3-carboxamide |
| 6.043 | (3S,4R)-4-(5-chloro-1-methyl-pyrazol-3-yl)-N-(2,3-difluorophenyl)-1-methyl-2-oxo-pyrrolidine-3-carboxamide |
| 6.044 | (3S,4R)-4-(5-chloro-1-methyl-pyrazol-3-yl)-N-(2-fluorophenyl)-1-methyl-2-oxo-pyrrolidine-3-carboxamide |
| 6.045 | (3S,4R)-4-(5-chloro-1-methyl-pyrazol-3-yl)-N-(2,4-difluorophenyl)-1-methyl-2-oxo-pyrrolidine-3-carboxamide |
| 6.046 | (3S,4R)-4-(5-chloro-1-methyl-pyrazol-3-yl)-N-[3-fluoro-2-(trifluoromethoxy)phenyl]-1-methyl-2-oxo-pyrrolidine-3-carboxamide |
| 6.047 | (3S,4R)-4-(5-chloro-1-methyl-pyrazol-3-yl)-N-[3-fluoro-2-(trifluoromethyl)phenyl]-1-methyl-2-oxo-pyrrolidine-3-carboxamide |
| 6.048 | (3S,4R)-4-(5-chloro-1-methyl-pyrazol-3-yl)-N-(3-fluoro-2-methoxy-phenyl)-1-methyl-2-oxo-pyrrolidine-3-carboxamide |
| 6.049 | (3S,4R)-4-(5-chloro-1-methyl-pyrazol-3-yl)-1-methyl-2-oxo-N-(2,3,4-trifluorophenyl)pyrrolidine-3-carboxamide |
| 6.050 | (3S,4R)-4-(5-chloro-1-methyl-pyrazol-3-yl)-N-(2,6-difluoro-3-pyridyl)-1-methyl-2-oxo-pyrrolidine-3-carboxamide |
| 6.051 | (3S,4R)-4-(5-chloro-1-methyl-pyrazol-3-yl)-N-(6-fluoro-2-pyridyl)-1-methyl-2-oxo-pyrrolidine-3-carboxamide |
| 6.052 | (3S,4R)-4-(5-chloro-1-methyl-pyrazol-3-yl)-N-[2-(difluoromethoxy)-3-fluoro-phenyl]-1-methyl-2-oxo-pyrrolidine-3-carboxamide |
| 6.053 | (3S,4R)-4-(5-chloro-1-methyl-pyrazol-3-yl)-N-(2-ethylphenyl)-1-methyl-2-oxo-pyrrolidine-3-carboxamide |
| 6.054 | (3S,4R)-4-(4-bromo-5-chloro-1-methyl-pyrazol-3-yl)-N-[2-(1,1-difluoroethyl)-3-fluoro-phenyl]-1-methyl-2-oxo-pyrrolidine-3-carboxamide |
| 6.055 | (3S,4R)-4-(5-chloro-1-methyl-pyrazol-3-yl)-N-(2-chloro-3-thienyl)-1-methyl-2-oxo-pyrrolidine-3-carboxamide |
| 6.056 | (3S,4R)-4-(5-chloro-1-methyl-pyrazol-3-yl)-N-(2-fluoro-3-thienyl)-1-methyl-2-oxo-pyrrolidine-3-carboxamide |
| 6.057 | (3S,4S)-4-(5-chloro-1-methyl-pyrazol-4-yl)-N-(2,3-difluorophenyl)-1-methyl-2-oxo-pyrrolidine-3-carboxamide |
| 6.058 | (3S,4S)-4-(5-chloro-1-methyl-pyrazol-4-yl)-N-(2-fluorophenyl)-1-methyl-2-oxo-pyrrolidine-3-carboxamide |
| 6.059 | (3S,4S)-4-(5-chloro-1-methyl-pyrazol-4-yl)-N-(2,4-difluorophenyl)-1-methyl-2-oxo-pyrrolidine-3-carboxamide |
| 6.060 | (3S,4S)-4-(5-chloro-1-methyl-pyrazol-4-yl)-N-[3-fluoro-2-(trifluoromethoxy)phenyl]-1-methyl-2-oxo-pyrrolidine-3-carboxamide |
| 6.061 | (3S,4S)-4-(5-chloro-1-methyl-pyrazol-4-yl)-N-[3-fluoro-2-(trifluoromethyl)phenyl]-1-methyl-2-oxo-pyrrolidine-3-carboxamide |
| 6.062 | (3S,4S)-4-(5-chloro-1-methyl-pyrazol-4-yl)-N-(3-fluoro-2-methoxy-phenyl)-1-methyl-2-oxo-pyrrolidine-3-carboxamide |
| 6.063 | (3S,4S)-4-(5-chloro-1-methyl-pyrazol-4-yl)-1-methyl-2-oxo-N-(2,3,4-trifluorophenyl)pyrrolidine-3-carboxamide |
| 6.064 | (3S,4S)-4-(3-bromo-5-chloro-1-methyl-pyrazol-4-yl)-N-(2,6-difluoro-3-pyridyl)-1-methyl-2-oxo-pyrrolidine-3-carboxamide |
| 6.065 | (3S,4S)-4-(5-chloro-1-methyl-pyrazol-4-yl)-N-(6-fluoro-2-pyridyl)-1-methyl-2-oxo-pyrrolidine-3-carboxamide |
| 6.066 | (3S,4S)-4-(5-chloro-1-methyl-pyrazol-4-yl)-N-[2-(difluoromethoxy)-3-fluoro-phenyl]-1-methyl-2-oxo-pyrrolidine-3-carboxamide |
| 6.067 | (3S,4S)-4-(5-chloro-1-methyl-pyrazol-4-yl)-N-(2-ethylphenyl)-1-methyl-2-oxo-pyrrolidine-3-carboxamide |
| 6.068 | (3S,4S)-4-(5-chloro-1-methyl-pyrazol-4-yl)-N-[2-(1,1-difluoroethyl)-3-fluoro-phenyl]-1-methyl-2-oxo-pyrrolidine-3-carboxamide |

TABLE 6-continued

Compounds of formula (I1) as described herein

| Compound No. | Name |
|---|---|
| 6.069 | (3S,4S)-4-(5-chloro-1-methyl-pyrazol-4-yl)-N-(2-chloro-3-thienyl)-1-methyl-2-oxo-pyrrolidine-3-carboxamide |
| 6.070 | (3S,4S)-4-(5-chloro-1-methyl-pyrazol-4-yl)-N-(2-fluoro-3-thienyl)-1-methyl-2-oxo-pyrrolidine-3-carboxamide |
| 6.071 | (3S,4R)-4-(5-chloro-2-methyl-pyrazol-3-yl)-N-(2,3-difluorophenyl)-1-methyl-2-oxo-pyrrolidine-3-carboxamide |
| 6.072 | (3S)-4-(5-chloro-2-methyl-pyrazol-3-yl)-N-(2-fluorophenyl)-1-methyl-2-oxo-pyrrolidine-3-carboxamide |
| 6.073 | (3S,4R)-4-(5-chloro-2-methyl-pyrazol-3-yl)-N-(2,4-difluorophenyl)-1-methyl-2-oxo-pyrrolidine-3-carboxamide |
| 6.074 | (3S,4R)-4-(5-chloro-2-methyl-pyrazol-3-yl)-N-[3-fluoro-2-(trifluoromethoxy)phenyl]-1-methyl-2-oxo-pyrrolidine-3-carboxamide |
| 6.075 | (3S,4R)-4-(5-chloro-2-methyl-pyrazol-3-yl)-N-[3-fluoro-2-(trifluoromethyl)phenyl]-1-methyl-2-oxo-pyrrolidine-3-carboxamide |
| 6.076 | (3S,4R)-4-(5-chloro-2-methyl-pyrazol-3-yl)-N-(3-fluoro-2-methoxy-phenyl)-1-methyl-2-oxo-pyrrolidine-3-carboxamide |
| 6.077 | (3S,4R)-1-methyl-4-[2-methyl-5-(trifluoromethyl)pyrazol-3-yl]-2-oxo-N-(2,3,4-trifluorophenyl)pyrrolidine-3-carboxamide |
| 6.078 | (3S,4R)-N-(2,6-difluoro-3-pyridyl)-1-methyl-4-[1-methyl-3-(chorol)-3H-pyrazol-5-yl]-2-oxo-pyrrolidine-3-carboxamide |
| 6.079 | (3S,4R)-N-(6-fluoro-2-pyridyl)-1-methyl-4-[1-methyl-3-(chloro)-3H-pyrazol-5-yl]-2-oxo-pyrrolidine-3-carboxamide |
| 6.080 | (3S,4R)-N-[2-(difluoromethoxy)-3-fluoro-phenyl]-1-methyl-4-[1-methyl-3-(chloro)-3H-pyrazol-5-yl]-2-oxo-pyrrolidine-3-carboxamide |
| 6.081 | (3S,4R)-N-(2-ethylphenyl)-1-methyl-4-[1-methyl-3-(chloro)-3H-pyrazol-5-yl]-2-oxo-pyrrolidine-3-carboxamide |
| 6.082 | (3S,4R)-N-[2-(1,1-difluoroethyl)-3-fluoro-phenyl]-1-methyl-4-[1-methyl-3-(chloro)-3H-pyrazol-5-yl]-2-oxo-pyrrolidine-3-carboxamide |
| 6.083 | (3S,4R)-N-(2-chloro-3-thienyl)-1-methyl-4-[1-methyl-3-(chloro)-3H-pyrazol-5-yl]-2-oxo-pyrrolidine-3-carboxamide |
| 6.084 | (3S,4R)-N-(2-fluoro-3-thienyl)-1-methyl-4-[1-methyl-3-(chloro)-3H-pyrazol-5-yl]-2-oxo-pyrrolidine-3-carboxamide |
| 6.085 | (3S,4R)-4-(4-bromo-5-chloro-1-methyl-pyrazol-3-yl)-N-(2,3-difluorophenyl)-1-methyl-2-oxo-pyrrolidine-3-carboxamide |
| 6.086 | (3S,4R)-4-(4-bromo-5-chloro-1-methyl-pyrazol-3-yl)-N-(2-fluorophenyl)-1-methyl-2-oxo-pyrrolidine-3-carboxamide |
| 6.087 | (3S,4R)-4-(4-bromo-5-chloro-1-methyl-pyrazol-3-yl)-N-(2,4-difluorophenyl)-1-methyl-2-oxo-pyrrolidine-3-carboxamide |
| 6.088 | (3S,4R)-4-(4-bromo-5-chloro-1-methyl-pyrazol-3-yl)-N-[3-fluoro-2-(trifluoromethoxy)phenyl]-1-methyl-2-oxo-pyrrolidine-3-carboxamide |
| 6.089 | (3S,4R)-4-(4-bromo-5-chloro-1-methyl-pyrazol-3-yl)-N-[3-fluoro-2-(trifluoromethyl)phenyl]-1-methyl-2-oxo-pyrrolidine-3-carboxamide |
| 6.090 | (3S,4R)-4-(4-bromo-5-chloro-1-methyl-pyrazol-3-yl)-N-(3-fluoro-2-methoxy-phenyl)-1-methyl-2-oxo-pyrrolidine-3-carboxamide |
| 6.091 | (3S,4R)-4-(4-bromo-5-chloro-1-methyl-pyrazol-3-yl)-1-methyl-2-oxo-N-(2,3,4-trifluorophenyl)pyrrolidine-3-carboxamide |
| 6.092 | (3S,4R)-4-(4-bromo-5-chloro-1-methyl-pyrazol-3-yl)-N-(2,6-difluoro-3-pyridyl)-1-methyl-2-oxo-pyrrolidine-3-carboxamide |
| 6.093 | (3S,4R)-4-(4-bromo-5-chloro-1-methyl-pyrazol-3-yl)-N-(6-fluoro-2-pyridyl)-1-methyl-2-oxo-pyrrolidine-3-carboxamide |
| 6.094 | (3S,4R)-4-(4-bromo-5-chloro-1-methyl-pyrazol-3-yl)-N-[2-(difluoromethoxy)-3-fluoro-phenyl]-1-methyl-2-oxo-pyrrolidine-3-carboxamide |
| 6.095 | (3S,4R)-4-(4-bromo-5-chloro-1-methyl-pyrazol-3-yl)-N-(2-ethylphenyl)-1-methyl-2-oxo-pyrrolidine-3-carboxamide |
| 6.096 | (3S,4R)-4-(4-bromo-5-chloro-1-methyl-pyrazol-3-yl)-N-[2-(1,1-difluoroethyl)-3-fluoro-phenyl]-1-methyl-2-oxo-pyrrolidine-3-carboxamide |
| 6.097 | (3S,4R)-4-(4-bromo-5-chloro-1-methyl-pyrazol-3-yl)-N-(2-chloro-3-thienyl)-1-methyl-2-oxo-pyrrolidine-3-carboxamide |
| 6.098 | (3S,4R)-4-(4-bromo-5-chloro-1-methyl-pyrazol-3-yl)-N-(2-fluoro-3-thienyl)-1-methyl-2-oxo-pyrrolidine-3-carboxamide |
| 6.099 | (3S,4S)-4-(3-bromo-5-chloro-1-methyl-pyrazol-4-yl)-N-(2,3-difluorophenyl)-1-methyl-2-oxo-pyrrolidine-3-carboxamide |
| 6.100 | (3S,4S)-4-(3-bromo-5-chloro-1-methyl-pyrazol-4-yl)-N-(2-fluorophenyl)-1-methyl-2-oxo-pyrrolidine-3-carboxamide |
| 6.101 | (3S,4S)-4-(3-bromo-5-chloro-1-methyl-pyrazol-4-yl)-N-(2,4-difluorophenyl)-1-methyl-2-oxo-pyrrolidine-3-carboxamide |
| 6.102 | (3S,4S)-4-(3-bromo-5-chloro-1-methyl-pyrazol-4-yl)-N-[3-fluoro-2-(trifluoromethoxy)phenyl]-1-methyl-2-oxo-pyrrolidine-3-carboxamide |
| 6.103 | (3S,4S)-4-(3-bromo-5-chloro-1-methyl-pyrazol-4-yl)-N-[3-fluoro-2-(trifluoromethyl)phenyl]-1-methyl-2-oxo-pyrrolidine-3-carboxamide |
| 6.104 | (3S,4S)-4-(3-bromo-5-chloro-1-methyl-pyrazol-4-yl)-N-(3-fluoro-2-methoxy-phenyl)-1-methyl-2-oxo-pyrrolidine-3-carboxamide |
| 6.105 | (3S,4S)-4-(3-bromo-5-chloro-1-methyl-pyrazol-4-yl)-1-methyl-2-oxo-N-(2,3,4-trifluorophenyl)pyrrolidine-3-carboxamide |

TABLE 6-continued

Compounds of formula (I1) as described herein

| Compound No. | Name |
|---|---|
| 6.106 | (3S,4S)-4-(3-bromo-5-chloro-1-methyl-pyrazol-4-yl)-N-(2,6-difluoro-3-pyridyl)-1-methyl-2-oxo-pyrrolidine-3-carboxamide |
| 6.107 | (3S,4S)-4-(3-bromo-5-chloro-1-methyl-pyrazol-4-yl)-N-(6-fluoro-2-pyridyl)-1-methyl-2-oxo-pyrrolidine-3-carboxamide |
| 6.108 | (3S,4S)-4-(3-bromo-5-chloro-1-methyl-pyrazol-4-yl)-N-[2-(difluoromethoxy)-3-fluoro-phenyl]-1-methyl-2-oxo-pyrrolidine-3-carboxamide |
| 6.109 | (3S,4S)-4-(3-bromo-5-chloro-1-methyl-pyrazol-4-yl)-N-(2-ethylphenyl)-1-methyl-2-oxo-pyrrolidine-3-carboxamide |
| 6.110 | (3S,4S)-4-(3-bromo-5-chloro-1-methyl-pyrazol-4-yl)-N-[2-(1,1-difluoroethyl)-3-fluoro-phenyl]-1-methyl-2-oxo-pyrrolidine-3-carboxamide |
| 6.111 | (3S,4S)-4-(3-bromo-5-chloro-1-methyl-pyrazol-4-yl)-N-(2-chloro-3-thienyl)-1-methyl-2-oxo-pyrrolidine-3-carboxamide |
| 6.112 | (3S,4S)-4-(3-bromo-5-chloro-1-methyl-pyrazol-4-yl)-N-(2-fluoro-3-thienyl)-1-methyl-2-oxo-pyrrolidine-3-carboxamide |
| 6.113 | (3S,4R)-4-(4-bromo-5-chloro-2-methyl-pyrazol-3-yl)-N-(2,3-difluorophenyl)-1-methyl-2-oxo-pyrrolidine-3-carboxamide |
| 6.114 | (3S)-4-(4-bromo-5-chloro-2-methyl-pyrazol-3-yl)-N-(2-fluorophenyl)-1-methyl-2-oxo-pyrrolidine-3-carboxamide |
| 6.115 | (3S,4R)-4-(4-bromo-5-chloro-2-methyl-pyrazol-3-yl)-N-(2,4-difluorophenyl)-1-methyl-2-oxo-pyrrolidine-3-carboxamide |
| 6.116 | (3S,4R)-4-(4-bromo-5-chloro-2-methyl-pyrazol-3-yl)-N-[3-fluoro-2-(trifluoromethoxy)phenyl]-1-methyl-2-oxo-pyrrolidine-3-carboxamide |
| 6.117 | (3S,4R)-4-(4-bromo-5-chloro-2-methyl-pyrazol-3-yl)-N-[3-fluoro-2-(trifluoromethyl)phenyl]-1-methyl-2-oxo-pyrrolidine-3-carboxamide |
| 6.118 | (3S,4R)-4-(4-bromo-5-chloro-2-methyl-pyrazol-3-yl)-N-(3-fluoro-2-methoxy-phenyl)-1-methyl-2-oxo-pyrrolidine-3-carboxamide |
| 6.119 | (3S,4R)-4-(4-bromo-5-chloro-2-methyl-pyrazol-3-yl)-1-methyl-2-oxo-N-(2,3,4-trifluorophenyl)pyrrolidine-3-carboxamide |
| 6.120 | (3S,4R)-4-(4-bromo-3-chloro-1-methyl-3H-pyrazol-5-yl)-N-(2,6-difluoro-3-pyridyl)-1-methyl-2-oxo-pyrrolidine-3-carboxamide |
| 6.121 | (3S,4R)-4-(4-bromo-3-chloro-1-methyl-3H-pyrazol-5-yl)-N-(6-fluoro-2-pyridyl)-1-methyl-2-oxo-pyrrolidine-3-carboxamide |
| 6.122 | (3S,4R)-4-(4-bromo-3-chloro-1-methyl-3H-pyrazol-5-yl)-N-[2-(difluoromethoxy)-3-fluoro-phenyl]-1-methyl-2-oxo-pyrrolidine-3-carboxamide |
| 6.123 | (3S,4R)-4-(4-bromo-3-chloro-1-methyl-3H-pyrazol-5-yl)-N-(2-ethylphenyl)-1-methyl-2-oxo-pyrrolidine-3-carboxamide |
| 6.124 | (3S,4R)-4-(4-bromo-3-chloro-1-methyl-3H-pyrazol-5-yl)-N-[2-(1,1-difluoroethyl)-3-fluoro-phenyl]-1-methyl-2-oxo-pyrrolidine-3-carboxamide |
| 6.125 | (3S,4R)-4-(4-bromo-3-chloro-1-methyl-3H-pyrazol-5-yl)-N-(2-chloro-3-thienyl)-1-methyl-2-oxo-pyrrolidine-3-carboxamide |
| 6.126 | (3S,4R)-4-(4-bromo-3-chloro-1-methyl-3H-pyrazol-5-yl)-N-(2-fluoro-3-thienyl)-1-methyl-2-oxo-pyrrolidine-3-carboxamide |

TABLE 7

Compounds of formula (J) for use as described herein

| Cmpd. No | Name |
|---|---|
| 7.001 | 1-methyl-4-[1-methyl-5-(trifluoromethyl)pyrazol-3-yl]-2-oxo-pyrrolidine-3-carboxylic acid |
| 7.002 | 1-methyl-4-[1-methyl-5-(trifluoromethyl)pyrazol-4-yl]-2-oxo-pyrrolidine-3-carboxylic acid |
| 7.003 | 4-(5-chloro-1-methyl-pyrazol-3-yl)-1-methyl-2-oxo-pyrrolidine-3-carboxylic acid |
| 7.004 | 4-(5-chloro-1-methyl-pyrazol-4-yl)-1-methyl-2-oxo-pyrrolidine-3-carboxylic acid |
| 7.005 | 4-(5-chloro-2-methyl-pyrazol-3-yl)-1-methyl-2-oxo-pyrrolidine-3-carboxylic acid |
| 7.006 | 4-(4-bromo-5-chloro-1-methyl-pyrazol-3-yl)-1-methyl-2-oxo-pyrrolidine-3-carboxylic acid |
| 7.007 | 4-(4-bromo-5-chloro-2-methyl-pyrazol-3-yl)-1-methyl-2-oxo-pyrrolidine-3-carboxylic acid |
| 7.008 | 4-(3-bromo-5-chloro-1-methyl-pyrazol-4-yl)-1-methyl-2-pxo-pyrrolidine-3-carboxylic acid |

EXAMPLES

Example 1: Preparation of the Herbicidal Compound N-(2,3-difluorophenyl)-1-methyl-4-[1-methyl-5-(trifluoromethyl)pyrazol-3-yl]-2-oxo-pyrrolidine-3-carboxamide

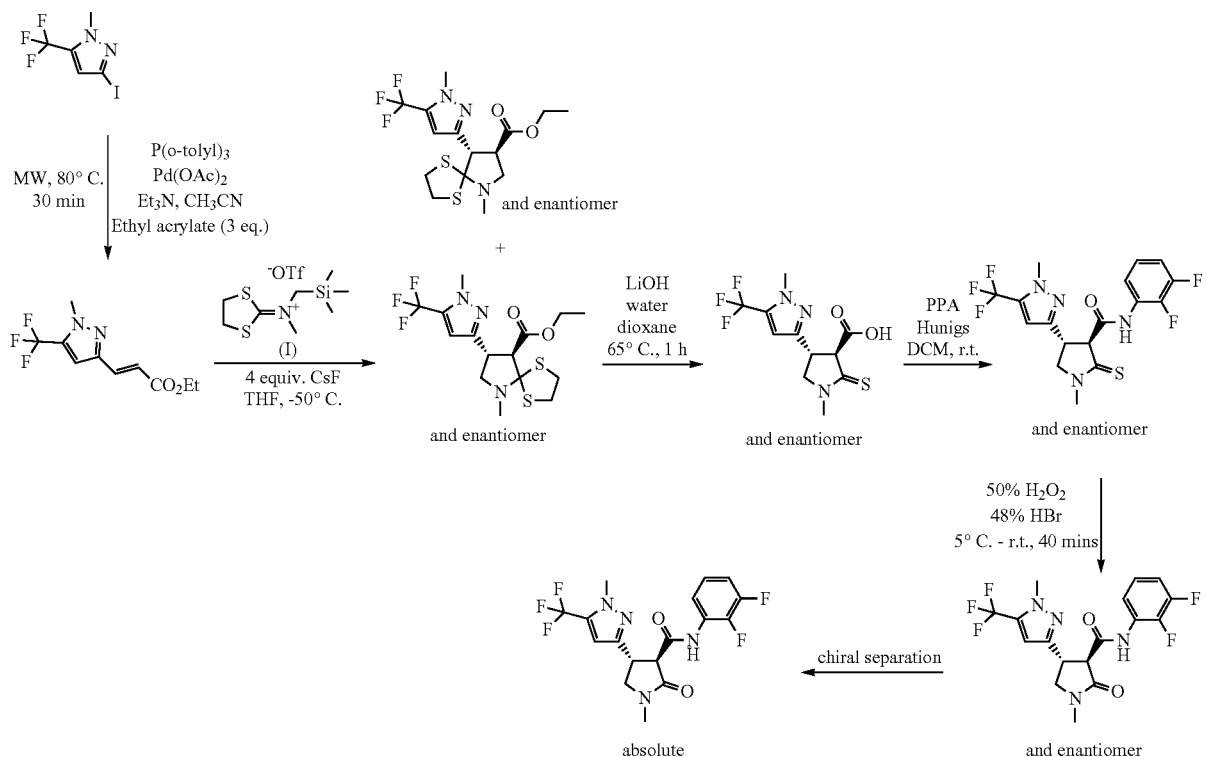

Salt (I) can be prepared as described in *Tetrahedron Lett.* 1995, 36, 9409.

Step 1 Ethyl (E)-3-[1-methyl-5-(trifluoromethyl)pyrazol-3-yl]prop-2-enoate

In a large microwave vial 3-iodo-1-methyl-5-(trifluoromethyl)pyrazole (3.62 mmol, 1.00 g) was dissolved in acetonitrile (15.2 mL), and ethyl acrylate (1.19 mL, 10.9 mmol), triethylamine (0.507 mL, 3.64 mmol), tri-ortho-tolylphosphine (0.362 mmol, 0.110 g) and palladium(II) acetate (0.362 mmol, 0.0813 g) were added, the air space above the stirred orange solution was swept with nitrogen, and the vial sealed and heated at 110° C. under microwave irradiation for 60 minutes. The reaction mixture was filtered (rinsing through with small portions of EtOAc), and the combined filtrate and washings were concentrated to remove the bulk of solvent. The residual orange-brown liquid was diluted with water (12 mL) and extracted with EtOAc (3×15 mL). The organic extracts were combined, washed with water (10 mL), passed through a phase separation cartridge then concentrated. Column chromatography (EtOAc/iso-hexane gradient elution) gave ethyl (E)-3-[1-methyl-5-(trifluoromethyl)pyrazol-3-yl]prop-2-enoate as a yellow oil, 0.51 g (57%).

$^1$H NMR: (400 MHz, CDCl$_3$): δ=7.58 (d, J=16.1 Hz, 1H), 6.81 (s, 1H), 6.43 (d, J=16.1 Hz, 1H), 4.26 (q, J=7.1 Hz, 2H), 4.01 (d, J=0.6 Hz, 3H), 1.33 (t, J=7.1 Hz, 3H).

Step 2 Ethyl-6-methyl-8-[1-methyl-5-(trifluoromethyl)pyrazol-3-yl]-1,4-dithia-6-azaspiro[4.4]nonane-9-carboxylate To a suspension of finely divided cesium fluoride (12.7 mmol, 1.93 g) in tetrahydrofuran (9.51 mL) stirred at −50° C., under a nitrogen atmosphere, was added a solution of ethyl (E)-3-[1-methyl-5-(trifluoromethyl)pyrazol-3-yl]prop-2-enoate (3.17 mmol, 0.787 g) and 1,3-dithiolan-2-ylidene-methyl-(trimethylsilylmethyl)ammonium;trifluoromethane-sulfonic acid (5.55 mmol, 2.06 g) in tetrahydrofuran (39.51 mL) drop-wise over approx. 15 minutes, keeping the reaction temperature below −45° C. The resulting very pale yellow cloudy suspension was allowed to warm slowly to room temperature and stirring was continued overnight. The reaction mixture was then diluted with DCM and filtered, washing through with further portions of DCM. The combined filtrate and washings were concentrated, and the crude material purified by column chromatography (EtOAc/cyclohexane gradient elution) giving ethyl-6-methyl-8-[1-methyl-5-(trifluoromethyl)pyrazol-3-yl]-1,4-dithia-6-azaspiro[4.4]nonane-9-carboxylate as a pale yellow oil, 566 mg (45%).

$^1$H NMR: (400 MHz, CDCl$_3$): δ=6.45 (s, 1H), 4.31-4.17 (m, 2H), 3.90 (d, J=0.6 Hz, 3H), 3.89-3.79 (m, 2H), 3.35-3.06 (m, 5H), 2.97-2.91 (m, 1H), 2.47 (s, 3H), 1.31 (t, J=7.2 Hz, 3H).

Step 3 1-Methyl-4-[1-methyl-5-(trifluoromethyl)pyrazol-3-yl]-2-thioxo-pyrrolidine-3-carboxylic Acid To a solution of ethyl 6-methyl-8-[1-methyl-5-(trifluoromethyl)pyrazol-3-yl]-1,4-dithia-6-azaspiro[4.4]nonane-9-carboxylate (1.43 mmol, 0.566 g) in dioxane (34.3 mL) and water (11.4 mL) was added LiOH (14.3 mmol, 0.343 g), and the stirred mixture heated to 60° C. under a nitrogen atmosphere for 1 hour. The reaction mixture was then allowed to cool to around 35° C. then concentrated to remove the bulk of dioxane. The residual mixture was diluted with water (10 mL), and partitioned between dilute HCl (5 mL, to pH3) and DCM (20 mL). The two-phase mixture was filtered to remove fine solids then the organic phase was separated. The aqueous was further extracted with DCM (2×15 mL), and all organic extracts combined, dried over $MgSO_4$, filtered and the filtrate concentrated giving 1-methyl-4-[1-methyl-5-(trifluoromethyl)pyrazol-3-yl]-2-thioxo-pyrrolidine-3-carboxylic acid as a light yellow solid, 399 mg (90%).

$^1$H NMR: (400 MHz, $CDCl_3$): δ=6.66 (s, 1H), 4.19-4.03 (m, 4H), 3.93 (d, J=0.5 Hz, 3H), 3.34 (s, 3H).

Step 4 N-(2,3-difluorophenyl)-1-methyl-4-[1-methyl-5-(trifluoromethyl)pyrazol-3-yl]-2-thioxo-pyrrolidine-3-carboxamide To a solution of 1-methyl-4-[1-methyl-5-(trifluoromethyl)pyrazol-3-yl]-2-thioxo-pyrrolidine-3-carboxylic acid (0.340 g, 1.11 mmol) in DCM (8.0 mL) was added 2,3-difluoroaniline (0.112 mL, 1.11 mmol) giving a pale yellow solution. Propylphosphonic anhydride (50 mass %) in ethyl acetate (1.88 mmol, 1.12 mL) was added, followed by the N,N-diisopropylamine (3.32 mmol, 0.578 mL) and the reaction mixture was stirred at room temperature for 1 hour. The reaction mixture was then quenched by the addition of water (2 mL) with stirring, transferred to a phase separation cartridge and the organics collected and concentrated. Column chromatography (EtOAc/iso-hexane gradient elution) gave N-(2,3-difluorophenyl)-1-methyl-4-[1-methyl-5-(trifluoromethyl)pyrazol-3-yl]-2-thioxo-pyrrolidine-3-carboxamide as a colourless crystalline solid, 264 mg (57%).

$^1$H NMR: (400 MHz, $CDCl_3$): δ=10.25 (br s, 1H), 8.01 (tdd, J=1.6, 6.6, 8.3 Hz, 1H), 7.04 (ddt, J=2.1, 5.9, 8.3 Hz, 1H), 6.94-6.86 (m, 1H), 6.58 (s, 1H), 4.40 (td, J=6.3, 8.6 Hz, 1H), 4.20 (d, J=6.4 Hz, 1H), 4.13 (dd, 1H), 4.00 (dd, 1H), 3.93 (d, 3H), 3.33 (s, 3H).

Step 5 N-(2,3-difluorophenyl)-1-methyl-4-[1-methyl-5-(trifluoromethyl)pyrazol-3-yl]-2-oxo-pyrrolidine-3-carboxamide To a solution of N-(2,3-difluorophenyl)-1-methyl-4-[1-methyl-5-(trifluoromethyl)pyrazol-3-yl]-2-thioxo-pyrrolidine-3-carboxamide (0.621 mmol, 0.260 g) in acetonitrile (6.21 mL) stirred and cooled to around 0 to −5° C., in an ice-salt bath, was added 50% hydrogen peroxide (0.746 mL) drop-wise and a white suspension resulted. After 5 minutes 45% aq. hydrobromic acid (0.0750 mL, 0.621 mmol) was added drop-wise and after stirring for 10 minutes the mixture was allowed to warm to room temperature. After 3 hours the reaction mixture was re-cooled to 5° C., and quenched with sodium thiosulfate solution (~10 mL). The mixture was diluted with EtOAc (15 mL) and water (10 mL), and the organic phase separated. The aqueous was further extracted with EtOAc (2×10 mL), then the organic extracts were combined, run through a phase separation cartridge then concentrated giving a colourless gum. Column chromatography (EtOAc/iso-hexane gradient elution) gave N-(2,3-difluorophenyl)-1-methyl-4-[1-methyl-5-(trifluoromethyl)pyrazol-3-yl]-2-oxo-pyrrolidine-3-carboxamide as a white crystalline solid, 210 mg (84%).

$^1$H NMR: (400 MHz, $CDCl_3$): δ=10.15 (br s, 1H), 8.04 (dd, J=6.6, 8.3 Hz, 1H), 7.06-6.99 (m, 1H), 6.89 (br dd, J=1.1, 8.6 Hz, 1H), 6.69 (s, 1H), 4.09 (q, 1H), 3.94 (s, 3H), 3.78 (d, J=9.5 Hz, 1H), 3.76-3.65 (m, 2H), 2.98 (d, 3H).

The racemic N-(2,3-difluorophenyl)-1-methyl-4-[1-methyl-5-(trifluoromethyl)pyrazol-3-yl]-2-oxo-pyrrolidine-3-carboxamide could be separated to afford the enantiomers (3S,4R)—N-(2,3-difluorophenyl)-1-methyl-4-[1-methyl-5-(trifluoromethyl)pyrazol-3-yl]-2-oxo-pyrrolidine-3 carboxamide and (3R,4S)—N-(2,3-difluorophenyl)-1-methyl-4-[1-methyl-5-(trifluoromethyl)pyrazol-3-yl]-2-oxo-pyrrolidine-3-carboxamide using a Chiralpak IA, 10×250 mm, 5 μm column with sc-$CO_2$ (solvent A) B=Isopropanol (solvent B) as solvents under isocratic conditions: 85% solvent A:15% solvent B at 15 mL/min.

Examples of further herbicidal compounds of formula (I) were made using the methods and compounds of the invention described herein, in a directly analogous manner to N-(2,3-difluorophenyl)-1-methyl-4-[1-methyl-5-(trifluoromethyl)pyrazol-3-yl]-2-oxo-pyrrolidine-3-carboxamide as described in Example 1 above. The structures and characteristic NMR data for these compounds are given below in Table 8.

TABLE 8

Herbicidal Compounds of formula (I) prepared using compounds and methods of the invention. Whilst the name of the preferred herbicidal enantiomer is given, in each case the NMR data corresponds to that for the respective racemate

| Compound No. | Structure (Compound of Formula (I1)) | 1HNMR ($CDCl_3$) |
| --- | --- | --- |
| 8.1 | (3S,4R)-N-(2,3-difluorophenyl)-1-methyl-4-[1-methyl-5-(trifluoromethyl)pyrazol-3-yl]-2-oxo-pyrrolidine-3-carboxamide | δ = 10.15 (br s, 1H), 8.04 (tdd, J = 1.6, 6.6, 8.3 Hz, 1H), 7.02 (ddt, J = 2.1, 5.9, 8.3 Hz, 1H), 6.93-6.85 (m, 1H), 6.69 (s, 1H), 4.09 (q, 1H), 3.94 (s, 3H), 3.81-3.65 (m, 3H), 2.98 (d, 3H) |
| 8.2 | (3S,4R)-N-(2-fluorophenyl)-1-methyl-4-[1-methyl-5-(trifluoromethyl)pyrazol-3-yl]-2-oxo-pyrrolidine-3-carboxamide | δ = 10.04 (br s, 1H), 8.31-8.25 (m, 1H), 7.13-7.00 (m, 3H), 6.69 (s, 1H), 4.11 (q, 1H), 3.94(s, 3H), 3.80-3.65 (m, 3H), 2.98 (d, 3H) |

TABLE 8-continued

Herbicidal Compounds of formula (I) prepared using compounds and methods of the invention. Whilst the name of the preferred herbicidal enantiomer is given, in each case the NMR data corresponds to that for the respective racemate

| Compound No. | Structure (Compound of Formula (I1)) | 1HNMR (CDCl$_3$) |
| --- | --- | --- |
| 8.3 | (3S,4R)-N-(2,4-difluorophenyl)-1-methyl-4-[1-methyl-5-(trifluoromethyl)pyrazol-3-yl]-2-oxo-pyrrolidine-3-carboxamide | δ = 9.98 (br s, 1H), 8.22 (dt, J = 6.0, 8.9 Hz, 1H), 6.90-6.80 (m, 2H), 6.69 (s, 1H), 4.09 (q, 1H), 3.94 (d, 3H), 3.80-3.65 (m, 3H), 2.97 (d, J = 0.7 Hz, 3H) |
| 8.4 | (3S,4R)-N-[3-fluoro-2-(trifluoromethoxy)phenyl]-1-methyl-4-[1-methyl-5-(trifluoromethyl)pyrazol-3-yl]-2-oxo-pyrrolidine-3-carboxamide | δ = 10.40 (s, 1H), 8.17 (td, J = 1.5, 8.5 Hz, 1H), 7.26-7.19 (m, 1H), 6.92 (ddd, J = 1.4, 8.4, 9.7 Hz, 1H), 6.69 (s, 1H), 4.07 (q, J = 9.0 Hz, 1H), 3.94 (s, 3H), 3.77 (d, 1H), 3.74-3.64 (m, 2H), 2.98 (s, 3H) |
| 8.5 | (3S,4R)-N-[3-fluoro-2-(trifluoromethyl)phenyl]-1-methyl-4-[1-methyl-5-(trifluoromethyl)pyrazol-3-yl]-2-oxo-pyrrolidine-3-carboxamide | δ = 10.16 (br s, 1H), 7.99 (d, J = 8.3 Hz, 1H), 7.46 (dt, J = 6.0, 8.4 Hz, 1H), 7.00-6.92 (m, 1H), 6.68 (s, 1H), 4.09 (q, J = 8.9 Hz, 1H), 3.94 (s, 3H), 3.79-3.66 (m, 3H), 2.98 (d, 3H) |
| 8.6 | (3S,4R)-N-(3-fluoro-2-methoxy-phenyl)-1-methyl-4-[1-methyl-5-(trifluoromethyl)pyrazol-3-yl]-2-oxo-pyrrolidine-3-carboxamide | δ = 10.21 (s, 1H), 8.13 (td, J = 1.3, 8.4 Hz, 1H), 6.96 (dt, J = 5.7, 8.3 Hz, 1H), 6.81 (ddd, J = 1.5, 8.4, 11.1 Hz, 1H), 6.68 (s, 1H), 4.13 (q, J = 9.0 Hz, 1H), 4.03 (d, J = 1.7 Hz, 3H), 3.94 (d, 3H), 3.78-3.63 (m, 3H), 2.97 (d, J = 0.7 Hz, 3H) |
| 8.7 | (3S,4R)-1-methyl-4-[1-methyl-5-(trifluoromethyl)pyrazol-3-yl]-2-oxo-N-(2,3,4-trifluorophenyl)pyrrolidine-3-carboxamide | δ = 10.08 (br s, 1H), 8.01-7.94 (m, 1H), 6.92 (ddt, J = 2.4, 7.7, 9.7 Hz, 1H), 6.68 (s, 1H), 4.07 (q, 1H), 3.94 (s, 3H), 3.77 (d, 1H), 3.75-3.65 (m, 2H), 2.98 (d, 3H) |
| 8.8 | (3S,4R)-N-(2,6-difluoro-3-pyridyl)-1-methyl-4-[1-methyl-5-(trifluoromethyl)pyrazol-3-yl]-2-oxo-pyrrolidine-3-carboxamide | δ = 10.17 (br s, 1H), 8.83-8.76 (m, 1H), 6.80 (dd, J = 2.9, 8.6 Hz, 1H), 6.67 (s, 1H), 4.07 (q, J = 8.9 Hz, 1H), 3.95 (d, 3H), 3.83-3.65 (m, 3H), 2.98 (d, 3H) |
| 8.9 | (3S,4R)-N-(6-fluoro-2-pyridyl)-1-methyl-4-[1-methyl-5-(trifluoromethyl)pyrazol-3-yl]-2-oxo-pyrrolidine-3-carboxamide | δ = 10.04 (s, 1H), 8.01 (dd, J = 1.8, 7.9 Hz, 1H), 7.75 (q, J = 8.1 Hz, 1H), 6.65 (s, 1H), 6.64 (dd, 1H), 4.12 (q, J = 9.0 Hz, 1H), 3.94 (s, 3H), 3.77-3.61 (m, 3H), 2.96 (s, 3H) |
| 8.10 | (3S,4R)-N[2-(difluoromethoxy)-3-fluoro-phenyl]-1-methyl-4-[1-methyl-5-(trifluoromethyl)pyrazol-3-yl]-2-oxo-pyrrolidine-3-carboxamide | δ = 10.29 (s, 1H), 8.17 (td, J = 1.3, 8.4 Hz, 1H), 7.17 (dt, J = 5.9, 8.5 Hz, 1H), 6.89 (ddd, J = 1.3, 8.5, 10.0 Hz, 1H), 6.68 (s, 1H), 6.67 (t[large F coupling], 1H), 4.09 (q, J = 9.0 Hz, 1H), 3.94 (s, 3H), 3.78 (d, J = 9.5 Hz, 1H), 3.75-3.63 (m, 2H), 2.98 (m, 3H) |
| 8.11 | (3S,4R)-N-(2-ethylphenyl)-1-methyl-4-[1-methyl-5-(trifluoromethyl)pyrazol-3-yl]-2-oxo-pyrrolidine-3-carboxamide | δ = 9.73 (s, 1H), 8.05 (d, 1H), 7.34-7.27 (m, 1H), 7.22-7.16 (m, 1H), 7.10-7.05 (m, 1H), 6.72 (s, 1H), 4.17-4.07 (m, 1H), 3.94 (s, 3H), 3.77-3.66 (m, 3H), 2.97 (d, 3H), 2.77-2.65 (m, 2H), 1.27 (t, 3H) |
| 8.12 | (3S,4R)-N-[2-(1,1-difluoroethyl)-3-fluoro-phenyl]-1-methyl-4-[1-methyl-5-(trifluoromethyl)pyrazol-3-yl]-2-oxo-pyrrolidine-3-carboxamide | δ = 9.75 (br s, 1H), 8.11 (dd, J = 5.1, 9.0 Hz, 1H), 7.21 (dd, J = 2.9, 9.2 Hz, 1H), 7.13-7.06 (m, 1H), 6.67 (s, 1H), 4.13 (q, J = 8.9 Hz, 1H), 3.94 (s, 3H), 3.76-3.64 (m, 3H), 2.97 (s, 3H), 1.98 (t, 3H) |
| 8.43 | (3S,4R)-4-(5-chloro-1-methyl-pyrazol-3-yl)-N-(2,3-difluorophenyl)-1-methyl-2-oxo-pyrrolidine-3-carboxamide | δ = 10.14 (s, 1H), 8.09-7.97 (m, 1H), 7.08-6.97 (m, 1H), 6.92-6.82 (m, 1H), 6.27 (s, 1H), 4.10-3.97 (m, 1H), 3.88-3.75 (m, 1H), 3.80 (s, 3H), 3.74-3.60 (m, 2H), 2.95 (s, 3H). |
| 8.45 | (3S,4R)-4-(5-chloro-1-methyl-pyrazol-3-yl)-N-(2,4-difluorophenyl)-1-methyl-2-oxo-pyrrolidine-3-carboxamide | δ = 9.96 (brs, 1H), 8.28-8.18 (m, 1H), 6.91-6.77 (m, 2H), 6.27 (s, 1H), 4.05 (q, J = 9.0 Hz, 1H), 3.83-3.60 (m, 3H), 3.79 (s, 3H), 2.96 (s, 3H) |

TABLE 8-continued

Herbicidal Compounds of formula (I) prepared using compounds and methods of the invention. Whilst the name of the preferred herbicidal enantiomer is given, in each case the NMR data corresponds to that for the respective racemate

| Compound No. | Structure (Compound of Formula (I1)) | 1HNMR (CDCl₃) |
| --- | --- | --- |
| 8.49 | (3S,4R)-4-(5-chloro-1-methyl-pyrazol-3-yl)-1-methyl-2-oxo-N-(2,3,4-trifluorophenyl)pyrrolidine-3-carboxamide | δ = 10.06 (s, 1H), 8.03-7.93 (m, 1H), 6.98-6.85 (m, 1H), 6.27 (s, 1H), 4.03 (q, 1H), 3.83-3.60 (m, 3H), 3.80 (s, 3H), 2.97 (s, 3H). |

The invention claimed is:

1. A compound of formula (B)

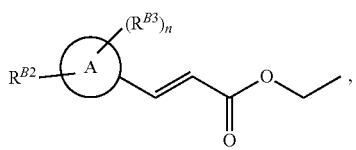

(B)

wherein,
ring A is $A^7$:

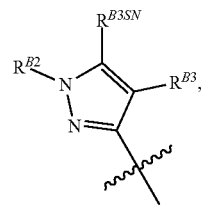

$A^7$ $R^{B2}$ is $C_1$-$C_3$ alkyl or $C_1$-$C_3$fluoroalkyl;
each $R^{B3}$ is independently halogen, $C_1$-$C_3$haloalkoxy, $C_1$-$C_3$alkoxy, $C_1$-$C_3$haloalkyl, or $C_1$-$C_3$alkyl; and
$R^{B3SN}$ is independently halogen, $C_1$-$C_3$haloalkoxy, $C_1$-$C_3$alkoxy, $C_1$-$C_3$haloalkyl, or $C_1$-$C_3$alkyl.

2. The compound of claim 1, wherein $R^{B2}$ is selected from the group consisting of methyl, ethyl, n-propyl, fluoromethyl, trifluoromethyl, fluoroethyl, difluoroethyl and trifluoroethyl.

3. The compound of claim 1, wherein $R^{B2}$ is selected from the group consisting of methyl, ethyl, and difluoroethyl.

4. The compound of claim 1, wherein $R^{B3}$ and $R^{B3SN}$ are each independently selected from chloro, fluoro, bromo, methyl, ethyl, difluoromethyl, trifluoromethyl, $C_1$-$C_3$haloalkoxy, and $C_1$-$C_3$alkoxy.

5. The compound of claim 1, wherein $R^{B2}$ is selected from the group consisting of methyl, ethyl, n-propyl, fluoromethyl, trifluoromethyl, fluoroethyl, difluoroethyl and trifluoroethyl.

6. The compound of claim 1, wherein $R^{B2}$ is selected from the group consisting of methyl, ethyl, and difluoroethyl.

7. The compound of claim 1, wherein $R^{B3}$ and $R^{B3SN}$ are each independently selected from chloro, fluoro, bromo, methyl, ethyl, difluoromethyl, trifluoromethyl, $C_1$-$C_3$haloalkoxy, and $C_1$-$C_3$alkoxy.

8. The compound of claim 1, wherein $C_1$-$C_3$haloalkyl is $C_1$-$C_3$fluoroalkyl.

9. The compound of claim 1, wherein $R^{B2}$ is selected from the group consisting of methyl, ethyl, and difluoroethyl; and $R^{B3}$ and $R^{B3SN}$ are independently selected from chloro, fluoro, bromo, methyl, ethyl, difluoromethyl, and trifluoromethyl.

10. A compound selected from:
ethyl (E)-3-[1-methyl-5-(trifluoromethyl)pyrazol-3-yl]prop-2-enoate;
ethyl (E)-3-[1-methyl-5-(trifluoromethyl)pyrazol-4-yl]prop-2-enoate;
ethyl (E)-3-(5-chloro-1-methyl-pyrazol-3-yl)prop-2-enoate;
ethyl (E)-3-(5-chloro-2-methyl-pyrazol-3-yl)prop-2-enoate;
ethyl (E)-3-(4-bromo-5-chloro-1-methyl-pyrazol-3-yl)prop-2-enoate;
ethyl (E)-3-(4-bromo-5-chloro-2-methyl-pyrazol-3-yl)prop-2-enoate; and
ethyl (E)-3-(3-bromo-5-chloro-1-methyl-pyrazol-4-yl)prop-2-enoate.

* * * * *